(12) United States Patent
Pollak et al.

(10) Patent No.: US 8,277,727 B2
(45) Date of Patent: Oct. 2, 2012

(54) DEVICE AND METHOD FOR INACTIVATION AND/OR STERILIZATION USING PLASMA

(76) Inventors: Jerome Pollak, Verdun (CA); Michel Moisan, Outremont (CA)

(*) Notice: Subject to any disclaimer, the term of this patent is extended or adjusted under 35 U.S.C. 154(b) by 315 days.

(21) Appl. No.: 12/522,409

(22) PCT Filed: Jan. 9, 2008

(86) PCT No.: PCT/CA2008/000032
§ 371 (c)(1),
(2), (4) Date: Dec. 18, 2009

(87) PCT Pub. No.: WO2008/083480
PCT Pub. Date: Jul. 17, 2008

(65) Prior Publication Data
US 2010/0178198 A1 Jul. 15, 2010

Related U.S. Application Data

(60) Provisional application No. 60/884,344, filed on Jan. 10, 2007.

(51) Int. Cl.
*A61L 2/00* (2006.01)
*A61L 2/04* (2006.01)
*A61L 9/00* (2006.01)
*A61L 11/00* (2006.01)
*C23F 11/00* (2006.01)

(52) U.S. Cl. ........................................ 422/23

(58) Field of Classification Search .................. 422/22, 422/23, 1
See application file for complete search history.

(56) References Cited

U.S. PATENT DOCUMENTS

| 4,801,427 | A  |   | 1/1989  | Jacob    |         |
|-----------|----|---|---------|----------|---------|
| 5,200,146 | A  |   | 4/1993  | Goodman  |         |
| 5,476,634 | A  | * | 12/1995 | Bridges et al. | 422/22 |
| 7,432,470 | B2 | * | 10/2008 | Kumar et al.   | 219/121.59 |
| 7,700,039 | B2 | * | 4/2010  | Nagatsu  | 422/21 |

(Continued)

FOREIGN PATENT DOCUMENTS
WO   2004050128   6/2004

OTHER PUBLICATIONS

Moisan, M., Zakrzewski, Z., Patel, R., and Leprince, P. "A Waveguide-Based Launcher to Sustain Long Plasma Columns Through the Propagation of an Electromagnetic Surface Wave", Sep. 1984, IEEE Transactions on Plasma Science, vol. PS-12, No. 3, pp. 203-214.*

(Continued)

*Primary Examiner* — Regina M. Yoo
(74) *Attorney, Agent, or Firm* — Bereskin Parr LLP/S.E.N.C.R.L., s.r.l.

(57) ABSTRACT

The invention concerns a method of sterilization and/or inactivation of at least one surface of at least one contaminated object. The method being characterized in that one subjects the surface to the discharge plasma generated from an applicator of electromagnetic field of linear type, the plasma having a temperature and an absorbed power per unit of volume predetermined by the operating conditions, so as to sterilize the surface without significantly degrading it. The invention also concerns a device enabling the sterilization and/or inactivation of at least one surface of at least one contaminated object by means of a plasma. This method and this device can be used to sterilize or inactivate several types of objects, such as packages, films, metal plates, dielectric plates, prosthesis used in the medical field, etc.

22 Claims, 17 Drawing Sheets

U.S. PATENT DOCUMENTS

2004/0047762 A1* 3/2004 Masaoka et al. ............... 422/22
2005/0158206 A1* 7/2005 Moisan et al. ................. 422/23

OTHER PUBLICATIONS

Zakrzewski et al. "Plasma sources using long linear microwave field applicators: main features, classification and modelling", Plasma Sources Sci. Technol. 4 (1995), pp. 379-397.
Boudam et al., "Characterization of the flowing afterglows of an N2-O2 reduced-pressure discharge: setting the operating conditions to achieve a dominant late afterglow and correlating the NOβ UV intensity variation with the N and O atom densities", J. Phys. D: Appl. Phys. 40 (2007) 1694-1711.
Lerouge et al., "Effect of gas composition on spore mortality and etching during low-pressure plasma sterilization", Jourrnal of Biomedical and Material Research 51 (1999), pp. 128-135.
Bretagnol et al., "Surface Functionalization and Patterning Techniques to Design Interfaces for Biomedical and Biosensor Applications", Plasma Processes and Polymers 3 (2006), pp. 443-445.
Pollak J et al., "Long and uniform plasma columns generated by linear field-applicators based on stripline technology", Plasma Sources Sci Technol. 16 (2007), pp. 1-14.
Pollak J et al., "Plasma sterilization within long and narrow-bore dielectric tubes contaminated with stacked bacterial spores Plasma processes and polymers", Plasma Process. Polym. 2008, 5, pp. 14-25.
Ganachev et al., "Production and control of planar microwave plasmas for materials processing", Plasma Sources Sci. Technol. 11 (2002) A178—A190 PII: S0963.
Slinko et al., 1988, "On producing an extended microwave discharge at high pressure", Sov. Phy. Tech. Phys. 33, 363-365.
Bosisio et al. RG, Weissfloch CF and Wertheimer MR 1972 the large volume microwave plasma generator (LMP™): a new tool for research and industrial processing Journal of microwave power 7, 325-346.
Bosisio RG, Wertheimer MR and Weissfloch CF 1973 Generation of large volume microwave plasma Journal of physics E: scientific instruments 6, 628-630.
Sauvé G, Moisan M, Zakrzewski Z and Bishop CA 1995 Sustaining long linear uniform plasmas with microwaves using a leaky-wave (throughguide) field applicator IEEE Trans. on antennas and propagation 43, 248-256.
Bilgic Am, Engel U, Voges E, Kuckelheim M and Broekaert JAC 2000 a new low-power microwave plasma source using microstrip technology for atomic emission spectrometry Plasma Sources Sci. Technol. 9, 1-4.
Bass A, Chevalier C and Blades MW 2001 A capacitively coupled microplasma formed in a quartz wafer J. Anal. At. Spectrom. 16, 919-921.
Broekaert JAC 2002 The development of microplasma for spectrochimical analysis Anal. Bioanal. Chem. 182-187.
Iza F. and Hopwood JA 2003 Low-power microwave plasma source based on a microstrip split resonator IEEE transaction on plasma science 31, 782-787.
Iza F and Hopwood JA 2005 Split-ring resonator microplasma: microwave model, plasma impedance and power efficiency Plasma Sources Sci. Technol. 14, 397-406.
Schermer S, Bings NH, Bilgic AM, Stonies R, Voges E and Broekaert JAC 2003 an improved microstrip plasma for optical emission spectrometry of gaseous species Spectrochimica Acta A Part B 58, 1585-1596.
Stonies R, Schermer S, Voges E and Broekaert JAC 2004 A new small microwave plasma torch Plasma Sources Sci. Technol. 13, 604-611.
Harvey AF (1963) Microwave Engineering, Academic Press.
Moisan M and Pelletier J (2006) Physique des plasmas collisionnels, EDP Sciences.
Feichtinger J, Schulz A, Walker M. and Schumacher U 2003 Sterilisation with low-pressure microwave plasmas Surface and coating technology 174-175, 564-569.
Soloshenko IA, Tsiolko VV, Khomich VA, Shchedrin AI, Ryabtsev AV, Bazhenov VY and mikhno IL 2000 Sterilization of medical products in low-pressure glow discharges Plasma physics reports 26, 792-800.
Xu L, Nonaka H, Zhou Hy, Ogino A, Nagata T, Koide Y, Nanko S, Kurawaki I and Nagatsu M 2007 Characteristics of surface-wave plasma with air-simulated N2-O2 gas mixture for low-temperature sterilization J. Phys D: Appl. Phys. 40, 803-808.
Sato T, Miyahara T, Doib A, Ochiai S, Urayama T and Nakatani T 2006 Sterilization mechanism for *Escherichia coli* by plasma flow at atmospheric pressure Applied physics letters 89, 073902.
Munakata M, Saito M and Hieda K 1991 Inactivation action spectra of *Bacillus subtilis* spores in extended ultraviolet wavelengths(50-300 nm) obtained with synchrotron radiation Phocochemistry and Photobiology 54, 761-768.
Moisan M and Ricard A 1977 Density of metastable atoms in an argon plasma produced by an RF surface wave Canadian journal of physics 55, 1010-1012.
Santiago I and Calzada MD 2007 Population measurement of the 3p54s configuration levels in an argon microwave plasma at atmospheric pressure Applied spectroscopy 61, 725-733.
Moisan M, Barbeau J, Moreau S, Pelletier J, Tabrizian M and Yahia LH 2001 Low-temperature sterilization using gas plasmas: a review of the experiements and an analysis of the inactivation mechanisms International Journal of pharmaceuticis 226, 1-21.
Hury S, Vidal Dr, Desor F, Pelletier J and Lagarde T 1998 A parametric study of the destruction efficiency of *Bacillus* spores in low pressure oxygen-based plasmas Letters in applied microbiology 26, 417-421.
Xiong R, Xie G, Edmondson AE and sheard MA 1999 A mathematical model for bacterial inactivation International journal of food microbiology 46, 45-55.
Cerf O 1977 Tailing of survival curves of bacterial spores Journal of applied bacteriology 42, 1-19.

* cited by examiner

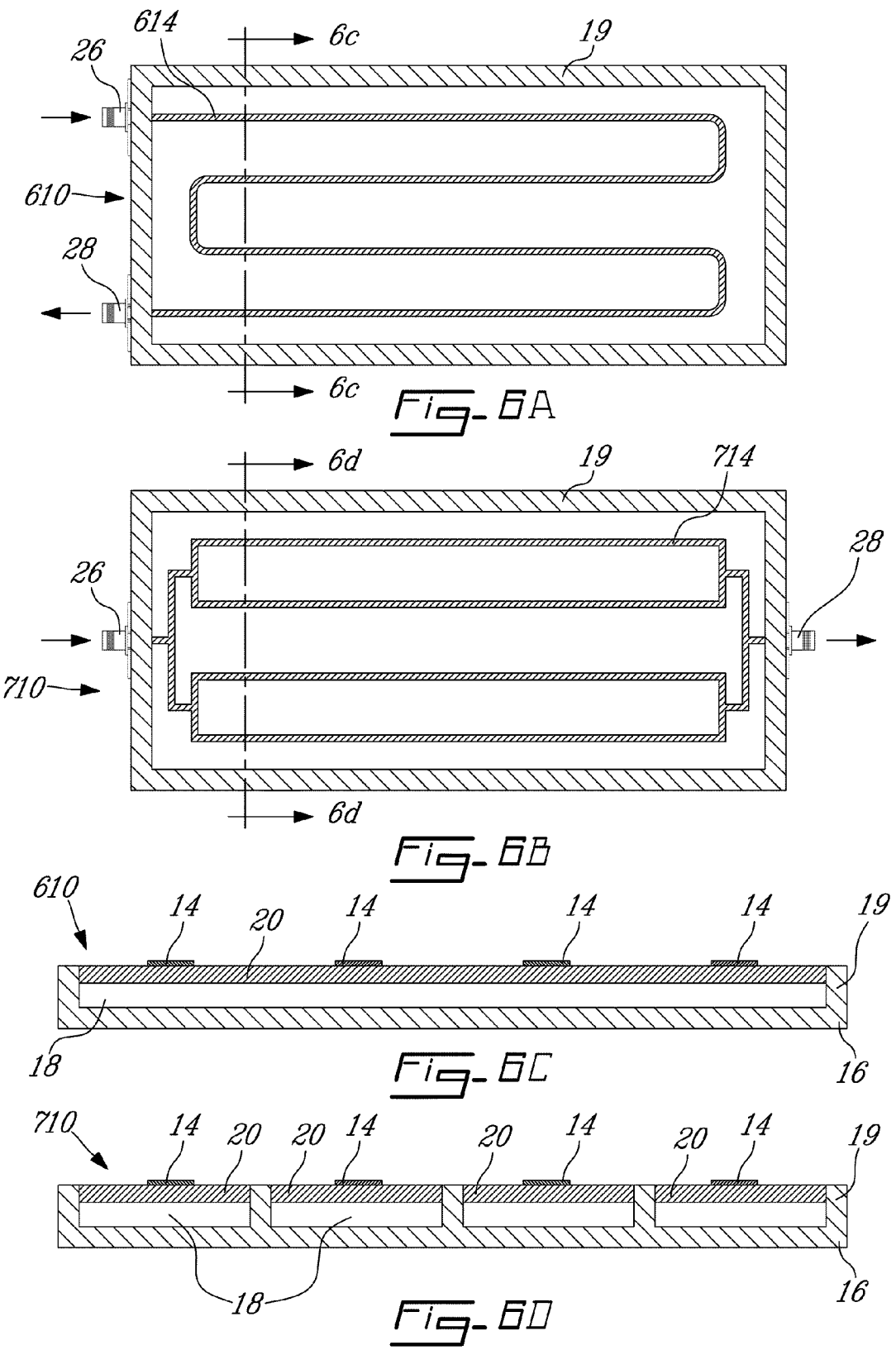

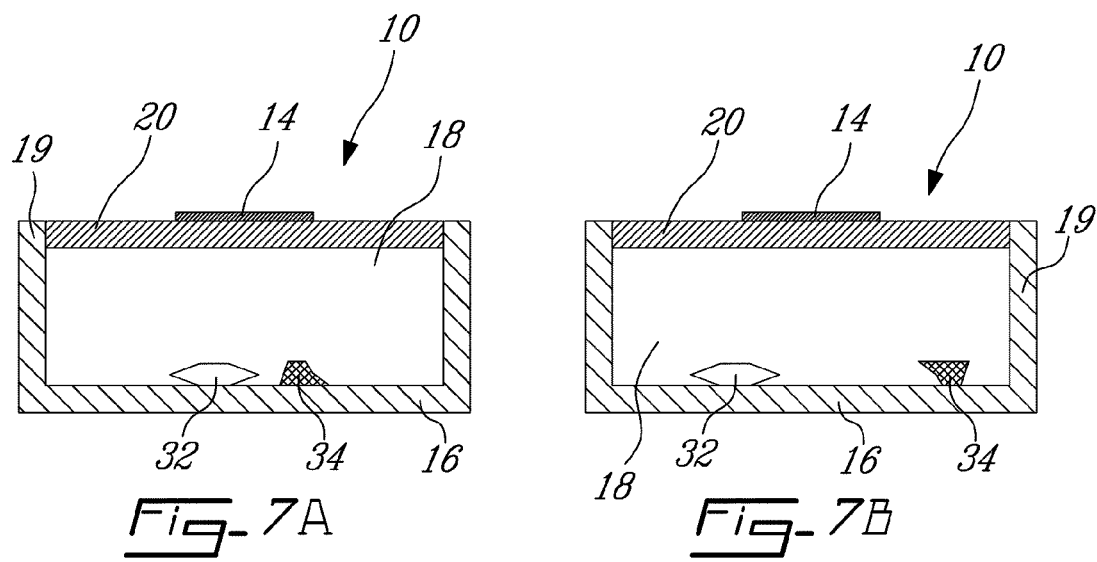
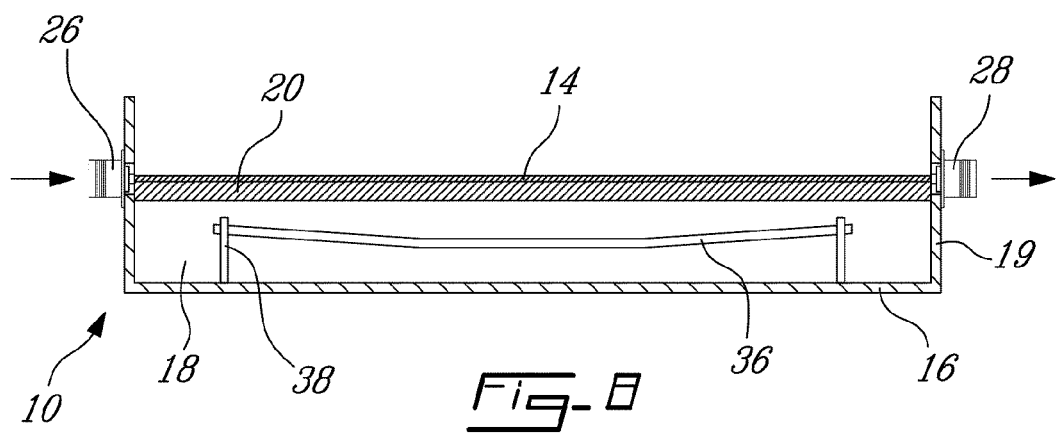

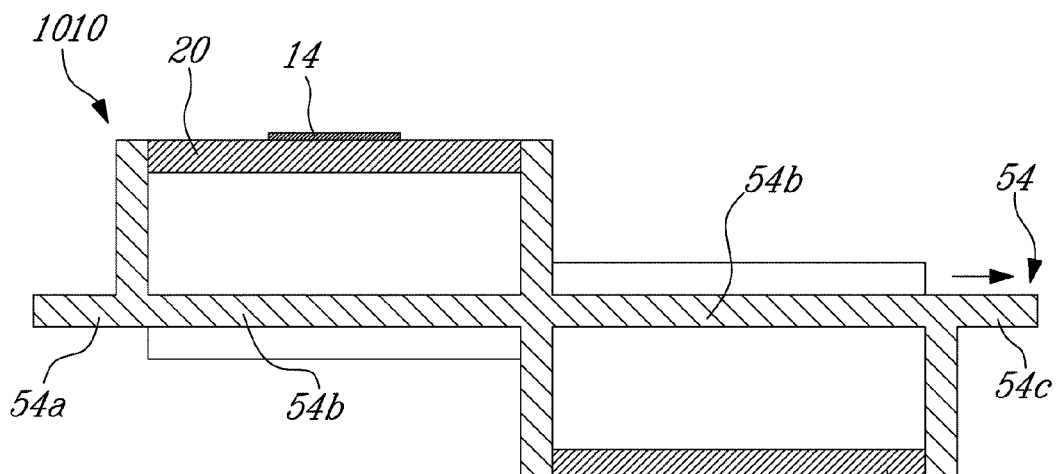
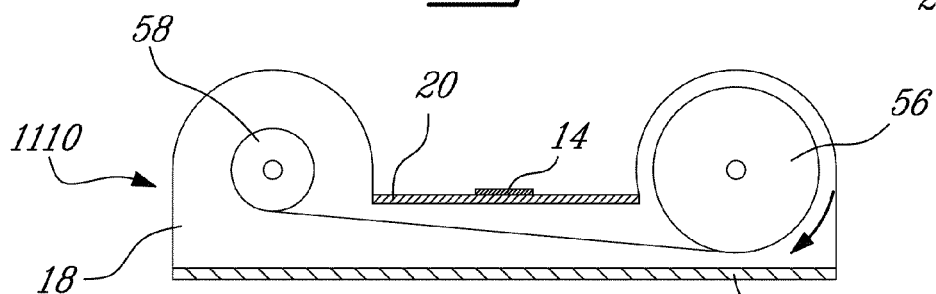
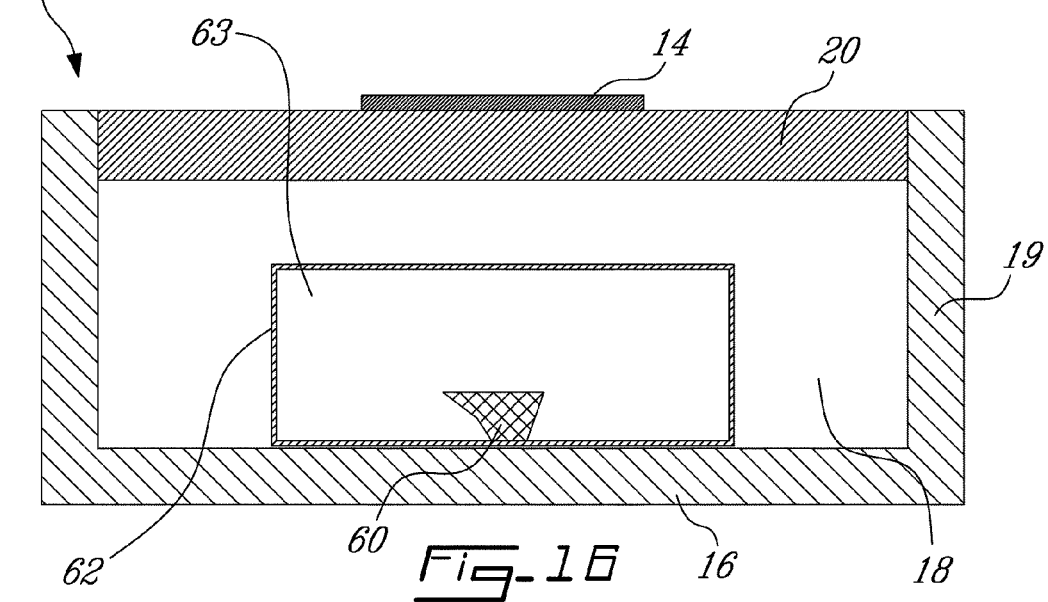

DEVICE AND METHOD FOR INACTIVATION AND/OR STERILIZATION USING PLASMA

CROSS-REFERENCE TO RELATED APPLICATION

This application claims the benefit of U.S. provisional application No. 60/844,344 filed on Jan. 10, 2007, which is hereby incorporated by reference in its entirety.

FIELD OF THE INVENTION

The present invention concerns the sterilization and/or inactivation by plasma of contaminated objects, such as those contaminated with micro-organisms. In particular, the invention concerns a method of plasma sterilization of various objects, such as three-dimensional objects.

BACKGROUND OF THE INVENTION

The field of sterilization of heat-sensitive three-dimensional objects continues to be the subject of much research. Traditionally, this sterilization is done by impregnating the objects being treated with fluids such as peracetic acid, glutaraldehyde, or hydrogen peroxide or by thermal treatments (dry or moist heat).

Plasma sterilization is emerging as a novel alternative to conventional sterilization techniques. Plasma sterilization offers promising features in terms of efficiency and reliability for inactivating micro-organisms. In addition, this technique can be made to operate at low temperatures (<50° C.), does not require venting time and is safe for the operators, patients and materials. The understanding of plasma sterilization is advancing rapidly, raising high scientific and commercial interests in the development of various types of plasma sterilizers. Nevertheless, no sterilizer making use of the plasma biocide species has yet been brought to the market place. Various reasons can be put forward to explain such a delay: 1) The level of damage induced on the various types of surfaces exposed to such a plasma treatment is an essential issue that has not yet been thoroughly assessed. In particular, as many medical devices (MDs) comprise polymers, the etching of polymers by such a process must be very small, allowing for many re-sterilization cycles. An alternative solution which would permit to avoid substantially degrading or damaging the MDs would be highly desirable. Moreover, variations in the hydrophobicity and biocompatibility of the processed surfaces (intended for limited or extended time of contact with tissues or body fluids) must be scrutinized. 2) Plasma sterilization of MDs must meet the requirements of hospital standards. In that respect, it is customary to sterilize MDs already enclosed in wrapping materials that protect them afterwards from external contamination during transportation and through storage time. However, the various wrapping materials presently used for that purpose are not compatible with a plasma afterglow sterilization process. This is because they strongly absorb UV radiation and also reduce the diffusion toward the MDs of the various plasma particles, namely atoms (e.g. oxygen radicals) and molecules (already present or newly formed), species that are eventually excited (becoming potential UV photon emitters) or ionised. An alternative solution which would permit the inactivation or sterilization of an object located inside a dielectric package would be highly desirable. 3) All parts of a MD should be exposed to substantially the same density or flux of the plasma species, which requires uniformity of the plasma biocide species everywhere in the sterilizer. As an example, consider the case of a plasma sterilizer filled with a large number of MDs: shadowing effects caused by an MD on a nearby other MD are possible, as well as local depletion of the active species (loading effect resulting, for instance, from surface recombination of the plasma species).

Several systems making use of the post-discharge of a plasma have recently been proposed. International application WO2004/050128 describes a method of plasma sterilization of objects of basically dielectric nature and containing a hollow part. In this document, the contaminated objects, and possibly also their packaging, are subjected alternately to the post-discharge of a plasma and to an electromagnetic field of sufficient intensity to create a plasma inside the hollow parts.

SUMMARY OF THE INVENTION

One aspect of the present invention relates to a method of sterilization and/or inactivation of at least one surface of at least one contaminated object. The method comprises submitting the at least one surface to a plasma discharge generated from an applicator of electromagnetic field of linear type. The plasma can have a temperature below 80° C., and an absorbed power per unit of volume of plasma of less than 20 W/L, so as to sterilize and/or inactivate the at least one surface without substantially degrading it.

Another aspect of the present invention concerns a device enabling the sterilization and/or inactivation of at least one surface of at least one contaminated object using a plasma. The device comprises:
 a chamber adapted to receive the object to be treated and a discharge of the plasma; and
 an applicator of electromagnetic field of linear type, adapted to generate the plasma discharge in the chamber so as to sterilize the at least one surface without damaging it in substantial manner.

It has been shown that this method and this device for sterilization and/or inactivation of objects can handle various objects, such as three-dimensional objects including but not limited to packaging films, dielectric or metallic plates, medical prosthesis and/or their packaging, etc. These objects are immersed in a plasma containing, for example, species (UV, radicals, ions) having bactericidal properties. The sterilization of these contaminated objects, such as objects contaminated by $10^6$ reference spores, is done quickly (for example, in less than 10 minutes or less than 1 minute) and at low temperature (e.g., temperature below 40° C.). Moreover, this method and device do not substantially degrade the objects being sterilized, it is nontoxic, and does not require any venting step after exposure to the plasma.

It was also observed that peculiar interesting features of the device and method of the present invention comprise a low gas temperature and a broadband impedance matching of the plasma source with no need for retuning, as well as stability and reproducibility of the discharge (non resonant behavior).

One or more three-dimensional object can be subjected directly to the bactericidal species of a plasma created in a chamber. This plasma can be engendered by an EM wave, propagating along the linear applicator. The plasma can occupy nearly all of the volume of the chamber, except for that taken up by the objects being sterilized. This plasma can be cold (e.g., a temperature below 40° C.) and thus it only slightly heats the objects being sterilized. This is a result of the low power absorbed per unit of volume of the plasma created (for example, less than 20 W/L).

When using the method and device of the present invention inactivation and/or sterilization can be carried out, for example, by subjecting the contaminated object to the discharge of the plasma for a period of less than 60 minutes, less than 30 minutes, less than 15 minutes, less than 10 minutes, less than 5 minutes, or less than 1 minute. The temperature of the plasma can be, for example, less than 70° C., less than 60° C., less than 50° C., less than 40° C., less than 35° C., less than 30° C., or less than 20° C. For example, the power absorbed per unit of volume of plasma can be less than 15 W/L, less than 10 W/L, or less than 5 W/L. The at least one object can be subjected to at least two treatments by the action of the discharge of the plasma: the object can be repositioned inside the chamber of the applicator of electromagnetic field of linear type between each treatment so as to treat all the surfaces of the object.

After a predetermined period of time, the power input and output of the applicator of electromagnetic field of linear type can be reversed so as to achieve a uniform treatment. The at least one surface can be treated in succession as it is introduced into the applicator. In such a case the object is in movement into the device and a portion is treated and when the portion is sterilized and/or inactivated, this portion exits the device and the successive portion is then treated.

The plasma can be generated by means of at least one high-frequency generator able to operate at a frequency of about 13.56 MHz to about 2.45 GHz or about 200 MHz to about 5.8 GHz. The plasma can comprise at least one rare gas for example argon. The plasma can also comprise $N_2$, $CO_2$, and/or $O_2$.

At least two objects can also be treated simultaneously by the plasma in the method and device of the invention. For example, the at least two objects can be treated simultaneously by the applicator, each of the objects being arranged, in the applicator, in a different chamber. The chambers can be insulated from each other. The same or different conditions of plasma generation can be applied in the chambers.

The at least one object being sterilized can be arranged in the sterilization chamber of the applicator so as to simultaneously sterilize all the outer surfaces of the object. Such an object can be, for example, a medical device, a dielectric film, such as agri-food industry packaging film or medical packaging film. For example, a film can be sterilized as it is rolled off. The film can be entering the chamber of the applicator at a predetermined height of the chamber, then leaving the chamber without interrupting the sterilization process or the electromagnetic power serving to maintain the plasma, the two surfaces of the dielectric film being then inactivated or sterilized simultaneously under the action of the bactericidal species of the plasma. For example, two dielectric films can be simultaneously inactivated or sterilized, then sealed in succession by thermal welding at certain spots.

The lower or upper surface of a dielectric plate, in contact with the plasma, can be disinfected or sterilized in succession. For example, a dielectric plate, such as one made of glass or fused silica, can move past inside the applicator, so that the lower surface and the upper surface of this dielectric plate can be inactivated or sterilized at the same time. The object to be treated can be a metal plate, moving past inside the applicator, so that the lower surface and the upper surface of this plate are inactivated or sterilized at the same time.

The at least one object can be sterilized directly inside its package (for example a film). The plasma can be created outside the object, as well as in a sufficient volume included between the package and the object.

Sterilization and/or inactivation of the at least one surface of the at least one object can be done without causing erosion to the surface. Determination of such an erosion-free treatment can be made by observing and comparing polystyrene micro-spheres by means of Scanning Electron Microscopy before and after sterilization and/or inactivation.

Sterilization and/or inactivation can be carried out in a chamber, and wherein at least one wall defining the chamber comprises at least one aperture so as to simultaneously permit treatment of at least one other object disposed outside of the chamber by means of a flowing afterglow of the plasma. The at least one wall can comprise a plurality of apertures, the apertures being adapted so as to prevent affecting propagation of an electromagnetic field along a transmission line. For example, the apertures can have a size which is at least three times inferior to the width of a conducting strip.

The applicator of electromagnetic field of linear type can comprise at least one conducting strip such as a metal strip extending from one end of the chamber to its opposite end. Alternatively, the applicator of electromagnetic field of linear type can comprise at least one metal strip having two opposite ends, the ends being in contact with a single one of the ends of the chamber. The strip can have an essentially constant width. Alternatively, the strip can have a width varying between the two ends. For example, the width of the strip can vary in an essentially increasing manner from an HF input to an output (load). The strip can include at least one curved portion. The applicator can further comprise a power divider. The field applicator can be an applicator of high-frequency field having a planar configuration. A planar transmission line can be used. For example a strip line, such as a three-plate line or a microstrip line can be used.

The geometry of the conducting strip and/or the ground plate of the applicator of electromagnetic field can be linear, circular, or of some other shape.

The sterilization chamber can comprise one or more dielectric supports to hold the objects being sterilized. The chamber can also comprise one conducting strip and at least one dielectric plate so as to insulate the strip from the plasma discharge.

The electromagnetic field applicator can be of distributed type. The latter can be formed by at least two planar transmission lines, each one extending for the entire length of the applicator. For example, there can be a network of linear applicators. The applicators can be compartmentalized so as to prevent risks of cross contamination between the various objects being sterilized and enabling treatments by different plasmas in each compartment.

The method and device of the present invention can comprise means for introducing the at least one object to be treated into the chamber for a predetermined period of time, and for removing it when sterility and/or inactivation is achieved.

The device and method of the present invention can be adapted to treat a moving object in continuous manner. They can comprise means for introducing at least one part of the at least one object to be treated into the chamber for a predetermined period of time, and for removing it when sterility and/or inactivation is achieved for this part. The means thus making it possible to treat the object in succession and in continuous manner.

At least one wall defining the chamber can be provided with at least one aperture adapted to permit a flowing afterglow of the plasma to diffuse outside the chamber. Such a configuration enables treatment of at least another object disposed outside the chamber. The at least one wall can comprise a plurality of apertures. The apertures are adapted so as to prevent affecting propagation of an electromagnetic field along the transmission line. The apertures can have a size which is at least three times inferior to the width of the conducting strip.

The distance between the conducting strip and an upper end and/or a bottom end of the chamber can be constant.

The distance between the conducting strip and an upper end and/or a bottom end of the chamber can be decreasing from an inlet to an outlet of the chamber.

The distance between the conducting strip and an upper end and/or a bottom end of the chamber can be variable from an inlet to an outlet of the chamber.

Various sterilized and/or inactivated objects can be obtained by implementing the method of the present invention and by using the device of the invention.

The present invention also involves a device comprising:
- a generator or a set of generators of high frequency (HF), able to operate at a frequency between 13.56 MHz and 2.45 GHz or 200 MHz and 5.8 GHz;
- a transmission line (e.g. a coaxial cable) able to transmit the power of the generator to the HF field applicator;
- a HF field applicator, of linear type, able to create a plasma from a gas (or gas mixture) subjected to its action;
- an adapted load, placed at the end of the line and serving to dissipate the power not used to maintain the plasma. In another mode of operation, this adapted load can be replaced by a short circuit or by a second power supply, coming from either the same generator or from another generator; and
- a detector of ultraviolet (UV) radiation.

The term HF can designate jointly radio and microwave frequencies.

The present invention can find application, for example, in the sterilization of heat-sensitive medical prosthesis. However, the invention is not limited to the field of sterilization of medical prosthesis. For example, it can also be applied to the disinfection or sterilization of plane surfaces in a moving process, for example, the surfaces being used in the food industry.

BRIEF DESCRIPTION OF THE FIGURES

The present invention can be illustrated without being limited to the following examples, in which:

FIGS. 6a and 6b schematically represent top views of various networks of linear applicators according to particular examples of the present invention, in which FIG. 6a represents a structure not containing a power divider system; FIG. 6b a structure containing a power divider system located inside the applicator; while FIGS. 6c and 6d represent, respectively, cross section views of devices of FIGS. 6a and 6b taken along lines 6c-6c and 6d-6d, wherein FIG. 6c shows a device with a single chamber, and FIG. 6d a device with partitioned compartments;

FIGS. 7a and 7b represent schematical cross section views of a system of sterilization of a three-dimensional object according to a particular example of the present invention, in 7b the object as well as its package have been turned over and shifted laterally and/or axially with respect to 7a;

FIG. 8 represents a schematical side view of the device allowing for sterilization of the external surfaces of a catheter or flexible endoscope, according to one particular example of the present invention;

FIG. 14 is a schematical representation of a device for inactivation or sterilization of the two surfaces of a metal plate as they move past, according to one particular example of the present invention;

FIG. 15 is a schematical representation of a device for inactivation or sterilization of the two surfaces of a dielectric film for packaging of agri-food products or medical products as they move past, according to one particular example of the present invention;

FIG. 16 is a schematical representation of a device for inactivation or sterilization of an object located inside a dielectric package according to one particular example of the present invention;

FIGS. 22a and 22b represent Scanned Electron Microscope (SEM) micrographs of polystyrene microspheres treated according to an embodiment of a method of the present invention using a device according to an embodiment of the present invention, wherein FIG. 22a shows the microspheres before treatment and FIG. 22b show the microspheres after treatment.

DETAILED DESCRIPTION OF THE INVENTION

The following examples are given to better define the present invention and should not be interpreted as limiting the present invention.

Planar Linear Applicators

The term linear applicator designates a particular class of electromagnetic field applicator. These are structures which extend for the entire length of the chamber comprising the plasma, as is described in the publication of Z. Zakrzewski and M. Moisan appearing in Plasma Sources Sci. Technol. 4, 379-397 (1995). There are many different linear applicators, in particular those using waveguide technology, and they make it possible to obtain plasmas having a good axial uniformity. Even so, this type of microwave transmission line only operates in a narrow band of operating frequencies, generally centered about 2.45 GHz or 915 MHz.

To take advantage of the axial uniformity offered by the linear applicators while making it possible to work in an extended band of operating frequencies, linear applicators based on planar transmission lines using the TEM mode (electric field and magnetic field perpendicular to the direction of propagation of the waves) have been developed.

Figure 1A:
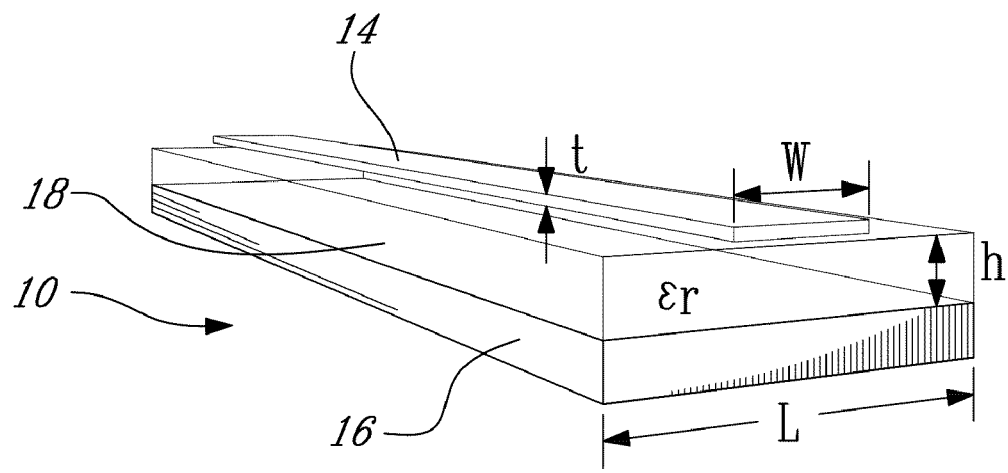
FIG. 1 shows a perspective view of a schematical representation of two devices according to particular examples of the present invention, in which the device comprises a microstrip line (1a) and a three-plate line (1b)
Figure 1B:
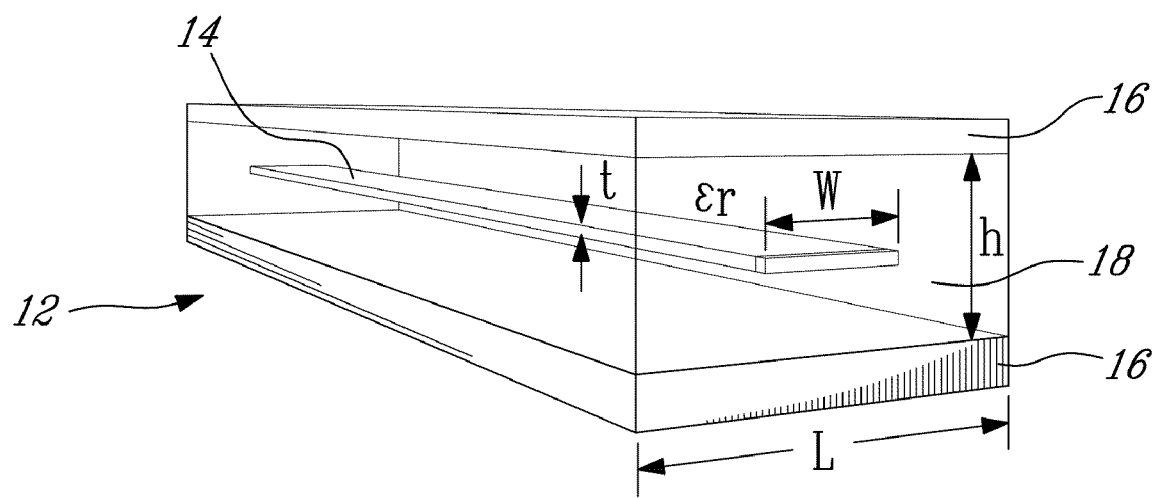

Among the different planar transmission lines, two types of strip lines have been developed. FIG. 1a shows a microstrip line 10 and FIG. 1b shows a three-plate line 12. The structures implemented are based on these two types of transmission line, the microstrip line (unsymmetrical line) and the stripline (symmetrical line). Striplines are also called "sandwich lines", "triplate lines", "symmetrical lines" or "double-ground-plane lines" Pollak J, Moisan M, Kéroack D and Boudam M K article to be published).

FIG. 1a shows the configuration and the characteristic dimensions of a microstrip line. A conducting strip 14 of width W and thickness t is located at a constant distance h above a conducting ground plate 16 of width L. A homogeneous dielectric medium 18 (for example air) of thickness h and relative permittivity $\in_r$ fills the entire region (or chamber) comprised between the ground plate and the conducting strip. Note that a microstrip line is not necessarily a microstructure as implied by its name; it is sometimes also called an "unsymmetrical line" or a "single-ground-plane line". FIG. 1b shows the configuration and characteristic dimensions of a stripline. A conducting strip 14 of width W and thickness t is centred between two parallel conducting ground plates 16 of width L and separated by a distance h. A homogeneous dielectric medium of relative permittivity $\in_r$ fills the entire region comprised between the parallel ground plates and the conducting strip.

Figure 2A:
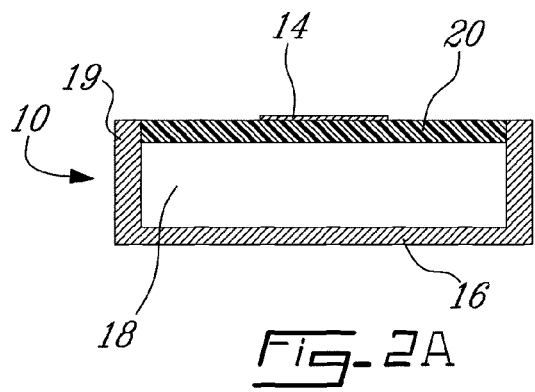
FIG. 2 shows a schematical cross section view of four different examples of devices of sterilization according to different embodiments of the present invention, the applicators in FIG. 2a and FIG. 2b having a microstrip line as defined in FIG. 1a, while the applicators in FIG. 2c and FIG. 2d have a three-plate line as defined in FIG. 1b.
Figure 2B:
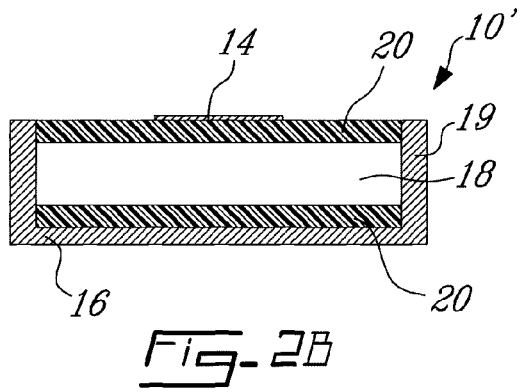
Figure 2C:
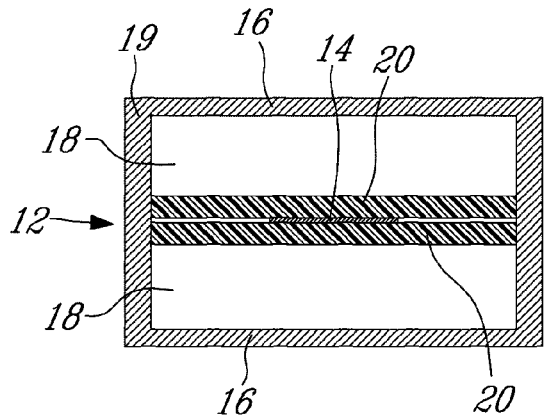
Figure 2D:
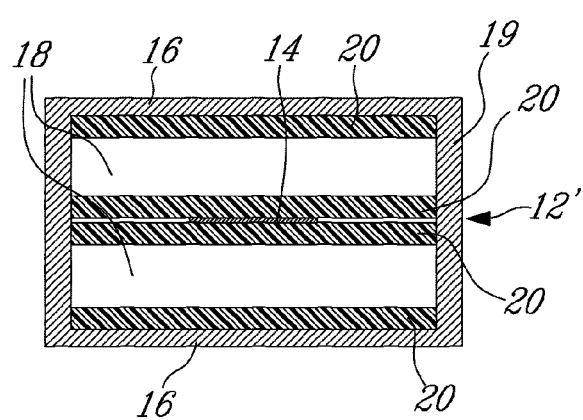

These new devices are represented in FIGS. 2a-d. The plasma sources based on the microstrip line (FIGS. 2a and 2b) are able to create a plasma in a single chamber 18 defined by a conducting frame 19, whereas it is possible to create plasmas in two different chambers with the plasma sources based on the three-plate line (FIGS. 2c and 2d). In this second configuration, the sterilization chambers are located on either side of the central conducting strip 14. FIGS. 2b and 2d represent variants of structures 2a and 2c, respectively. They use a second dielectric 20 plate between the plasma and the conducting ground plate or plates 16.

The dielectric plate 20 of FIG. 2a, transparent to the electromagnetic field (low loss factor), has the role of isolating the plasma from the surrounding air, which prevents contamination of the plasmagenic gas. It also makes it possible to avoid contact between the plasma and the central conducting strip. This plate can have a minimum thickness, depending on its length and its width, and letting it withstand exposure to vacuum without breaking. For example, the material used can be borosilicate glass (Pyrex®) due to its low cost price, its relative low loss factor, and its good physical and chemical behavior.

For powers less than about 300 W, the connections between the generator and the applicator and between the applicator and the matched load can make use of standard N connectors and coaxial cables with a low loss factor (for example, RG393/U). For higher powers and at high frequency (915 MHz or 2450 MHz), waveguide transitions to the linear applicator can be realized.

Figure 3:
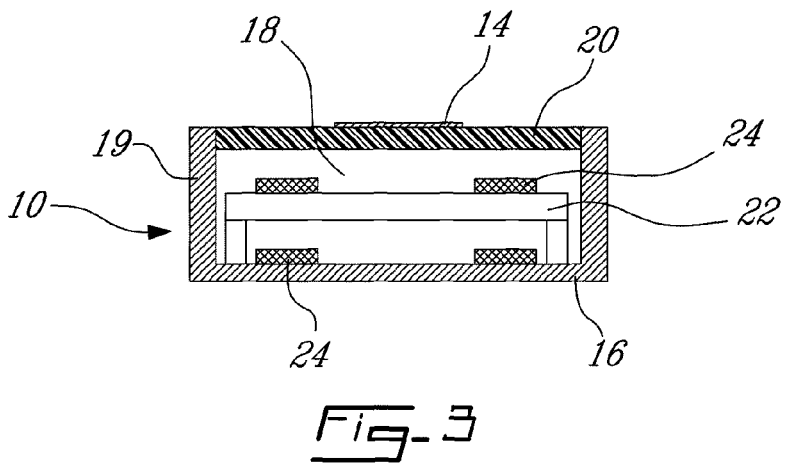
FIG. 3 shows a schematical cross section view of the linear applicator shown in FIG. 2a in which a dielectric support meant to hold one or more objects to be sterilized has been inserted in the sterilization chamber.

FIG. 3 shows the device 10 in which a dielectric support 22 has been inserted so as to hold objects 24 at a given height while other objects 24 remain on the conducting ground plate 16. It is possible to insert one or more dielectric supports inside the chamber 18.

Geometry and Configurations

For example, it is possible to use a linear applicator whose geometry and/or configuration varies along its length (FIGS. 4 and 5).

Figure 4A:
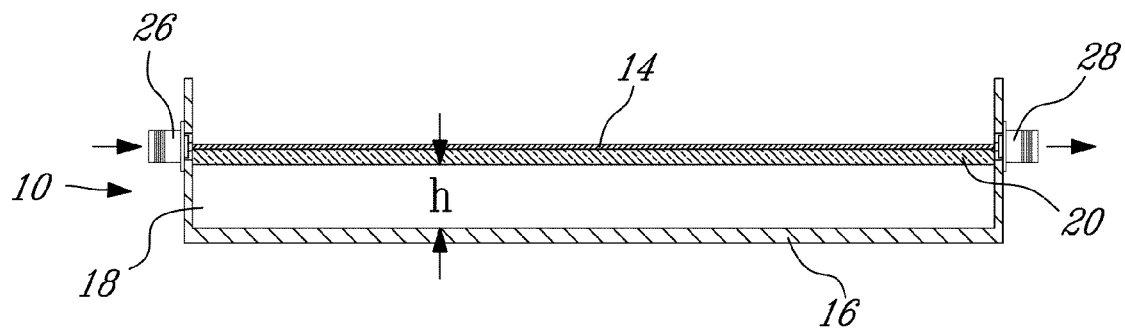
FIG. 4 shows a schematical cross section view of three sterilization devices according to different examples of the present invention, the three systems having different axial configurations of the ground conductor: 4a "classical" configuration with h constant; 4b "ramp" configuration where h varies as a linear function of the axial position, and 4c configuration where h varies axially in some way.
Figure 4B:
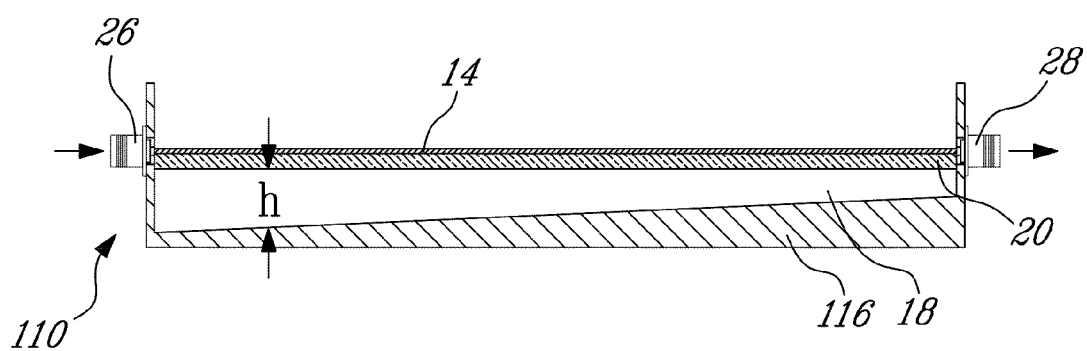
Figure 4C:
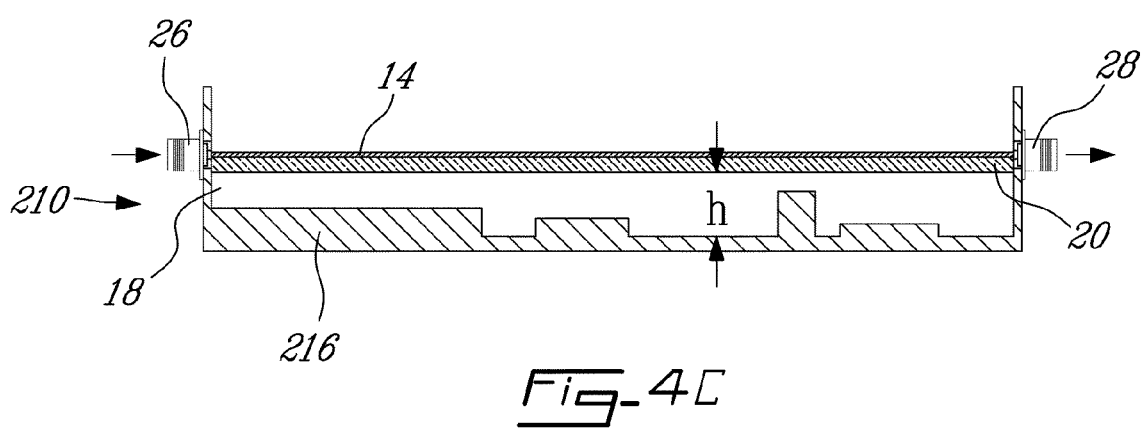

FIG. 4a shows a cross section view of a linear microstrip applicator of constant height h which has a conducting strip 14, a conducting ground plate 16, a chamber 18, a conducting frame 19, a dielectric plate 20, a HF power input 26, and a power output 28 (toward matched load). FIGS. 4b-4d have the same components with the exception of the geometry of the plate 16. FIGS. 4b and 4c are examples of linear applicators of variable height h. In FIG. 4b, the height of the conducting ground plate 116 decreases linearly along the length of the applicator, while in FIG. 4c the height h of the conducting ground plate 216 is some function of the axial position. It can thus be the that the distance (or height h) between the conducting strip and a bottom part of the chamber is constant (FIG. 4a), decreasing (FIG. 4b), or variable (FIG. 4c). The height or distance H in FIG. 9b (distance between the conducting strip 14 and an upper part of the device or frame) can also vary similarly to the various embodiments shown in FIGS. 4a, 4b and 4c. It was observed that by varying h or H it was possible to obtain a better axial uniformity of the plasma. It can also permit to adjust impedance of the plasma source in accordance with the transmission line impedance.

Figure 5A:
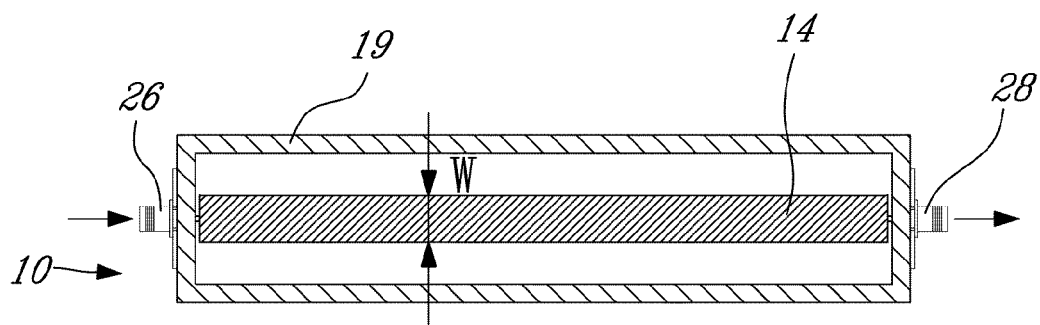
FIG. 5 shows a schematical top view of four different sterilization systems according to particular examples of the present invention, the systems having four different configurations of the central conducting strip: 5a constant width, 5b variable width, 5c any configuration, of constant width or not, and 5d circular geometry.
Figure 5B:
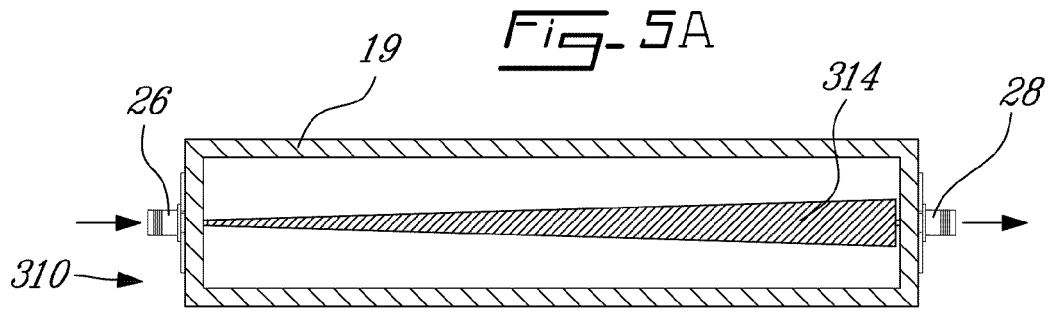
Figure 5C:
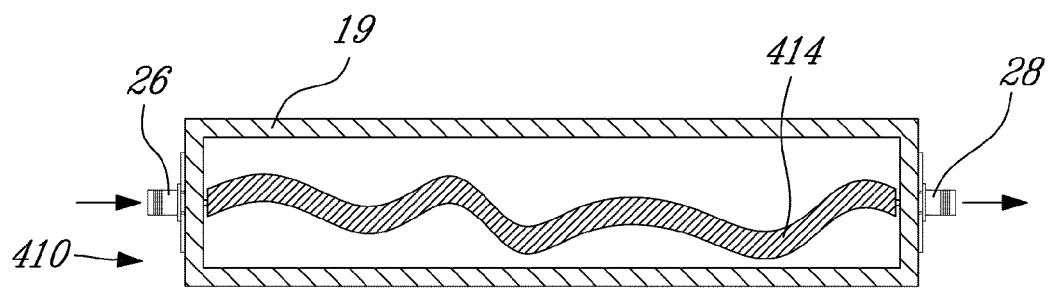
Figure 5D:
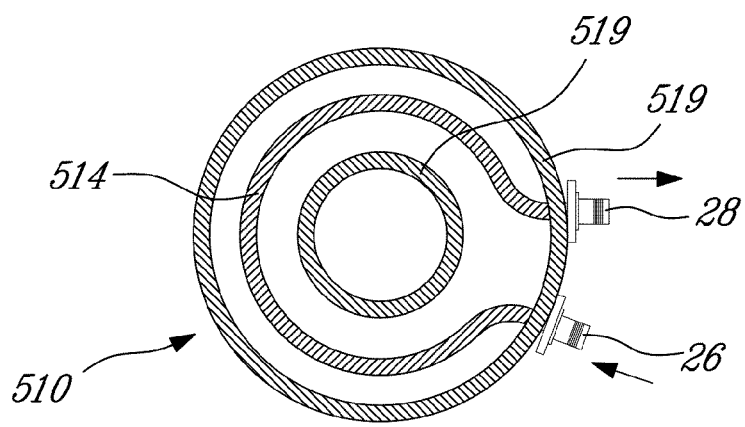

The central conducting strip 14 can also have several different geometries and/or configurations. FIG. 5a presents a top view of the applicator 10 whose central conducting strip 14 has a constant width W. The device 310 in FIG. 5b has a conducting strip 314 which has an increasing width. The width of conducting strip 414 in device 410 (FIG. 5c) varies along the structure. In another variant, a device 510 has a conducting strip 514 of circular geometry, as well as a metal frame 519 of circular geometry (FIG. 5d).

In fact, the geometry and configuration of the applicator depend basically on the application in question. In particular, when the three-dimensional object being sterilized has a complex structure, it can be useful to take advantage of the geometrical flexibility of microstrip or three-plate lines in order to adapt the shape of the applicator to that of the object being sterilized.

Modes of Utilization

Several different modes of utilization of the invention can be considered. For example, in the case when the residual power at the exit of the applicator is much lower than the incident power at the entry of the applicator, it is possible to reverse the input and output of power at the end of a particular time, so as to achieve a more uniform treatment along the length of the sterilization chamber. This reversal of the direction of power flow can be achieved with HF flip flops (switches).

In order to avoid any power losses, the matched load located at the end of the microwave line can be replaced by a short circuit (standing wave mode in the chamber). This method can prove useful, e.g., when a very high (or very low) intensity of electromagnetic field and/or concentration of sterilizing species is required at certain coordinates along the chamber.

In another example, the matched load located at the end of the applicator can be replaced by another HF power supply coming from either a second generator (with operating frequency equal to the first one, or not), or from the same generator. In the latter case, the power is previously divided (equally or not) at the output of the single generator.

It is also possible to use the HF power in pulsed mode in all the previously described modes of utilization, for example, in order to lower the temperature of the plasmagenic gas.

Length of the Structures

The length of the applicators can vary, for example, from a dozen centimeters up to several dozen meters. In fact, there is in theory no limit on the length of the plasma created by a linear applicator, except for the length of the linear structure and the power put out by the generator. This is an intrinsic feature of a linear applicator of HF field.

Width of the Structures

The width of the device can vary, for example, from several centimeters up to several meters. For example, in a device 710a sterilization chamber of large width can be filled with a plasma in its entirety by using several metal strips 714 spaced out along the structure (FIG. 6b) and arranged in parallel. For example, a single generator can feed power to all these linear applicators 610 by using a serpentine strip system 614 (FIG. 6a) or a power divider located inside or outside the applicator (not shown). When the linear applicator is based on a planar type transmission line, such as a microstrip line (FIG. 1a) or three-plate line (FIG. 1b), the power dividing system can be integrated in the linear applicator and be realized by the same transmission line technology (example with a microstrip line, FIG. 6b). Thus, this method makes it possible to optimize the invention in terms of packing density. Thus, several linear applicators based on a planar transmission line can easily be arranged in the form of a network, energized by a power divider system, which makes it possible to fill up a large lateral volume. The power divider system can be placed, for example, right inside the applicator, and it can divide the power by 2k, where k is an integer. FIGS. 6b and 6d illustrate this possibility with the example of a linear applicator formed by 4 conducting strips (k=2), which allows one to obtain a plasma source of larger lateral volume than with a linear applicator using a single metal strip. It should be noted that the total incident power needs to increase in proportion to the number of conducting strips used.

The distance between each strip cannot be less than a certain value, in order to avoid any interaction in the propagation of the EM waves between each of the strips. This distance also must not exceed a certain value in order to obtain a good lateral uniformity of the plasma so created. In fact, the optimal distance between each of the conducting strips basically depends on the height h between the conducting strips and the ground plane or planes, the width w of the strips, and the pressure of the gas.

FIG. 6d shows the use of a network of linear applicators with a compartmentalized sterilization chamber, that is, one divided into several lateral sections by tight walls extending over the entire length of the structure. The use of such a system can prove beneficial, for example, when one wishes to treat several objects at the same time, yet avoid any risk of a cross contamination between these different objects arranged separately in each compartment. This last configuration can also be of interest when one wishes to perform different treatments in each compartment. In particular, it is thus possible to inject mixtures of different plasmagenic gases in each of the compartments (both for the pressure and flow rate of the gases, and for the configuration of each linear applicator (see FIGS. 4 and 5)).

Depth of the Structures

Unlike for the length and the width of the linear applicators described in the present invention, there is a practical limit on the depth (height) of these structures. This limit results from the existence of modes of higher orders that can be excited above a maximum frequency, resulting in loss of certain of the properties of the applicator that require the presence of a TEM mode. For example, for the three-plate line, this value is given in the publication of I. J. Bahl and R. Garg appearing in Microwaves, pp. 90-96 (January 1978):

$$f_{max}(\text{GHz}) = \frac{15}{h\sqrt{\overset{\circ}{a}_r}} \frac{1}{\left(\frac{w}{h} + \frac{\partial}{4}\right)} \quad (5)$$

where w and h are in cm, w being the width of the central strip and h the distance between the conducting ground plates (FIG. 1b). It corresponds to the cutoff frequency of the first TE mode of higher order able to be excited.

Injection of Gases

The injection and evacuation of the plasmagenic gases in the sterilization chamber can be accomplished, for example, by means of openings located in the axis of the structure, through the lateral plates of the applicator, through the conducting ground plate or plates. It should be noted that once the openings intended for the injection and evacuation of the plasmagenic gases have been determined, it is still possible to reverse the direction of circulation of the plasmagenic gases for a more uniform treatment.

Positions of the Openings for Injection and Evacuation of Plasmagenic Gases

The injection and evacuation of the plasmagenic gases in the sterilization chamber can be achieved in various ways, by an appropriate modification of the geometry and/or the configuration (respective positions) of the gas inlet and outlet openings.

Figure 19:
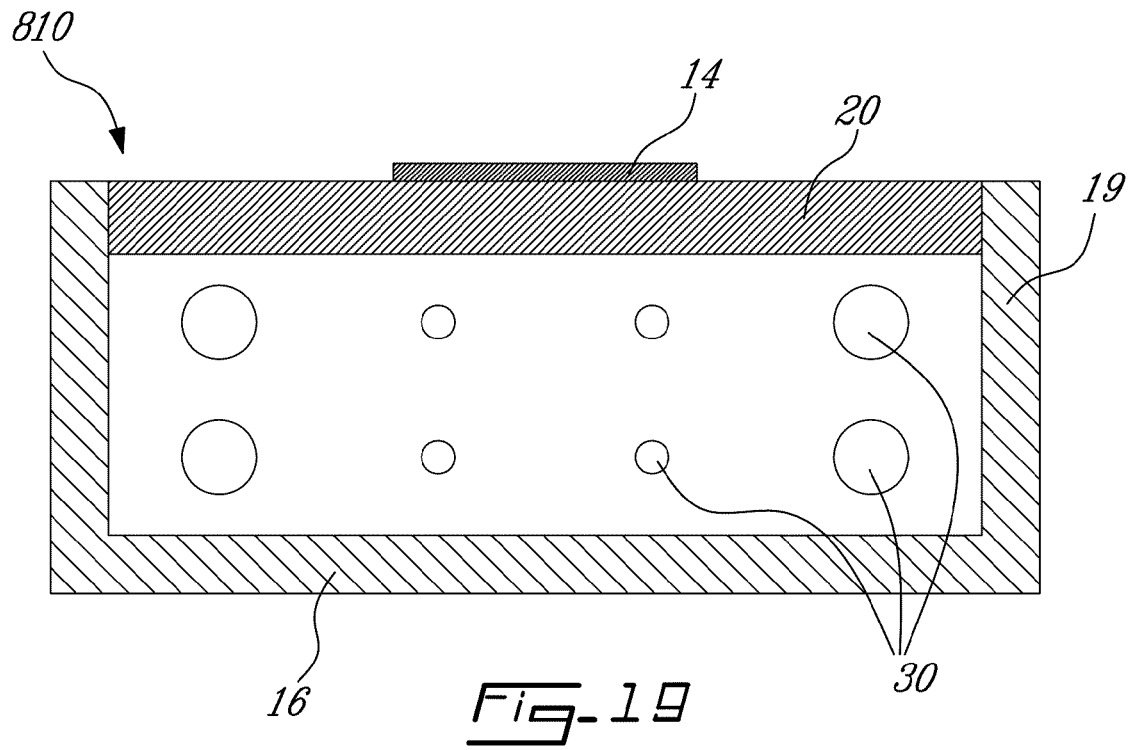
FIG. 19 is a schematical cross section view of the injection and evacuation planes of the plasmagenic gases of a sterilization device according to one particular example of the present invention in which the injection and the evacuation of the plasmagenic gases are realized by means of a network of circular holes situated parallel to the axis of the linear applicator.

According to one particular example of the invention, the gas flow is injected and evacuated by a network of openings 30 in the device (FIG. 19), in order to get a better lateral homogeneity of the plasma and, thus a more uniform treatment in the entire volume of the sterilization chamber. It can also be profitable to adjust separately the flow rate of plasmagenic gases circulating through each opening by using several flow meters or by modifying the geometry (and thus the hydrodynamic conductance) of the openings. For example, the evacuation rate of the plasmagenic gases is the lowest through openings of small diameter (FIG. 19).

Alternatively, the gas flow is evacuated by openings located beneath the objects being sterilized, so as to direct the flow of bactericidal species preferably onto them. This method can be of interest when one wishes to obtain a better inactivation rate or when the object being sterilized is made up of may layers of fibers (such as a mask or a bandage), forming a mesh impermeable to UV and too dense to enable the creation of the plasma between each of its meshes. It should be noted that in the case of a very dense mesh it may be of interest to stretch the object in one or more directions in the course of the sterilization procedure. This temporary modification of the structure of the object being sterilized should be reversible so that it does not lose certain of its intrinsic properties (such as its water-tightness).

Sterilization of Different Objects by Different Treatments

Figure 20:
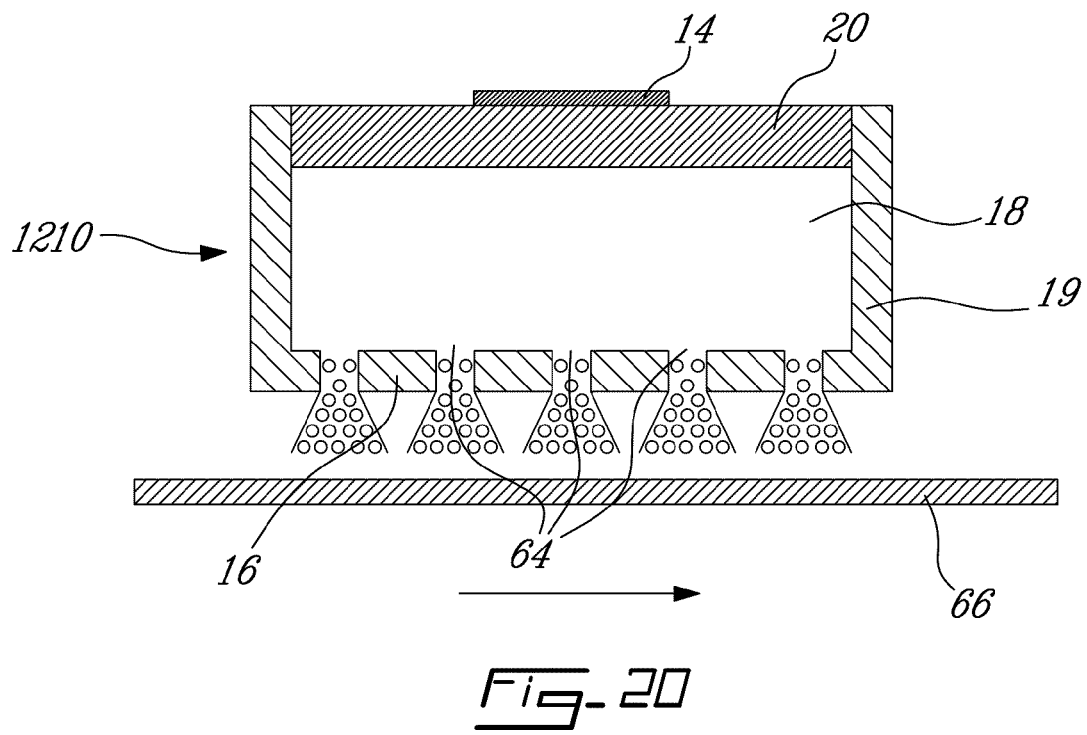
FIG. 20 shows a schematical cross section view of a device according to another example of the present invention, wherein a bottom part of the frame comprises a plurality of apertures so as to permit treatment of an object disposed outside the chamber by a flowing afterglow plasma passing therethrough.

As shown in FIG. 20, there is provided a device 1210 similar to device 10 shown in FIG. 2a, with the exception that the device 1210 is provided with a plurality of apertures 64. In fact, the conducting ground plate 16 is provided with such apertures so as to permit to simultaneously treat at least one other object 66 disposed outside of the chamber 18 by means of a flowing afterglow of the plasma. The apertures being adapted so as to prevent affecting propagation of the electromagnetic field along the transmission line. For example, the apertures can have a size which is at least three times inferior to the width of a conducting strip.

Procedure for the Sterilization of Three-Dimensional Objects

There is provided an example of general method that can be used so as to treat objects with the method and device of the present invention. In a first stage, the sterilization chamber does not contain any contaminated object. The chamber is then placed under vacuum, and the plasmagenic gas or gases are injected inside the chamber. Under the action of an EM field, a plasma is then created and all the interior surfaces of the chamber (especially the lower metal plate on which certain objects being sterilized may rest), which are thus in contact with the bactericidal species of the plasma, will be sterilized.

In a second stage, the object 34 to be treated are removed from their packaging 32 inside the chamber in a sterile environment. The object and also its packaging are arranged on the lower plate 16 of the sterilization device 10 (FIG. 7a). All the surfaces of the object 34 and the package 32 are in direct contact with the plasma are then sterilized, except for the surfaces of the objects in contact with the lower plate.

In a third stage (see FIG. 7b), the object 34 and its package 32 undergo a rotation, so as to sterilize the surfaces not so treated in the first stage, that is, those being in contact with the lower plate. The manipulation of the objects can be done inside the chamber by an operator provided with sterile gloves or an automated system (e.g., manipulator arms), whose ends designed to be in contact with the objects (to hold them) are sterile. It should be noted that at the end of the second stage certain surfaces of the chamber having been in contact with the object(s) (and/or the package(s)) being sterilized are not necessarily still sterile. This is why, after having been rotated, the objects, and possibly also their package, do not stay during the third stage in the same place in the chamber as during the second stage (compare FIGS. 7a and 7b): they are shifted axially and/or transversely inside the sterilization chamber. This process can be carried out, for example, by means of a rotary drum (rocker arm), made of a dielectric material (and thus transparent to the EM field) of low loss factor.

Alternatively, as shown in FIG. 8, the three-dimensional objects (for example object 36) to be sterilized, and possibly also their packaging (not shown), can be held by their ends at a certain height in the chamber 18 (e.g., at mid height), by means of sterile dielectric hooks 38 (such as Teflon), so as to simultaneously sterilize all the outer surfaces of the objects being treated, except for the surfaces in contact with the hooks. FIG. 8 illustrates one such possibility: this is a side view of a linear applicator where a medical prosthesis (such as a catheter or an endoscope) is held by its ends inside the sterilization chamber.

Sterilization Gas

The air initially present in the chamber can be evacuated down to a reduced pressure between 1.33 mPa and 133 Pa. A rare gas (e.g. argon) or a gas mixture (e.g. $N_2/O_2$) is then introduced into the sterilization chamber by means of one or more mass flow meters. The gas flow rate can be between 5 and 10,000 standard milliliters per minute (mLsm). At low pressure, for example, (<133 Pa), the HF power applied is enough to ignite the discharge, while at high pressure it is necessary to use a Tesla coil or a piezoelectric device to initiate it.

At the end of the cycle, after the time necessary to achieve sterility of the surfaces exposed to the bactericidal species of the plasma has expired, the return to atmospheric pressure is done in a few seconds by opening a valve with filter (sterile) having pores, for example, of about 0.22 μm.

HF Power Characteristics of the Planar Plasma Source

The power absorbed by the discharge $P_A$ as a function of the incident power $P_I$ when assuming a lossless field applicator is simply given here by:

$$P_A = P_I - P_R - P_T.$$

Figure 21A:
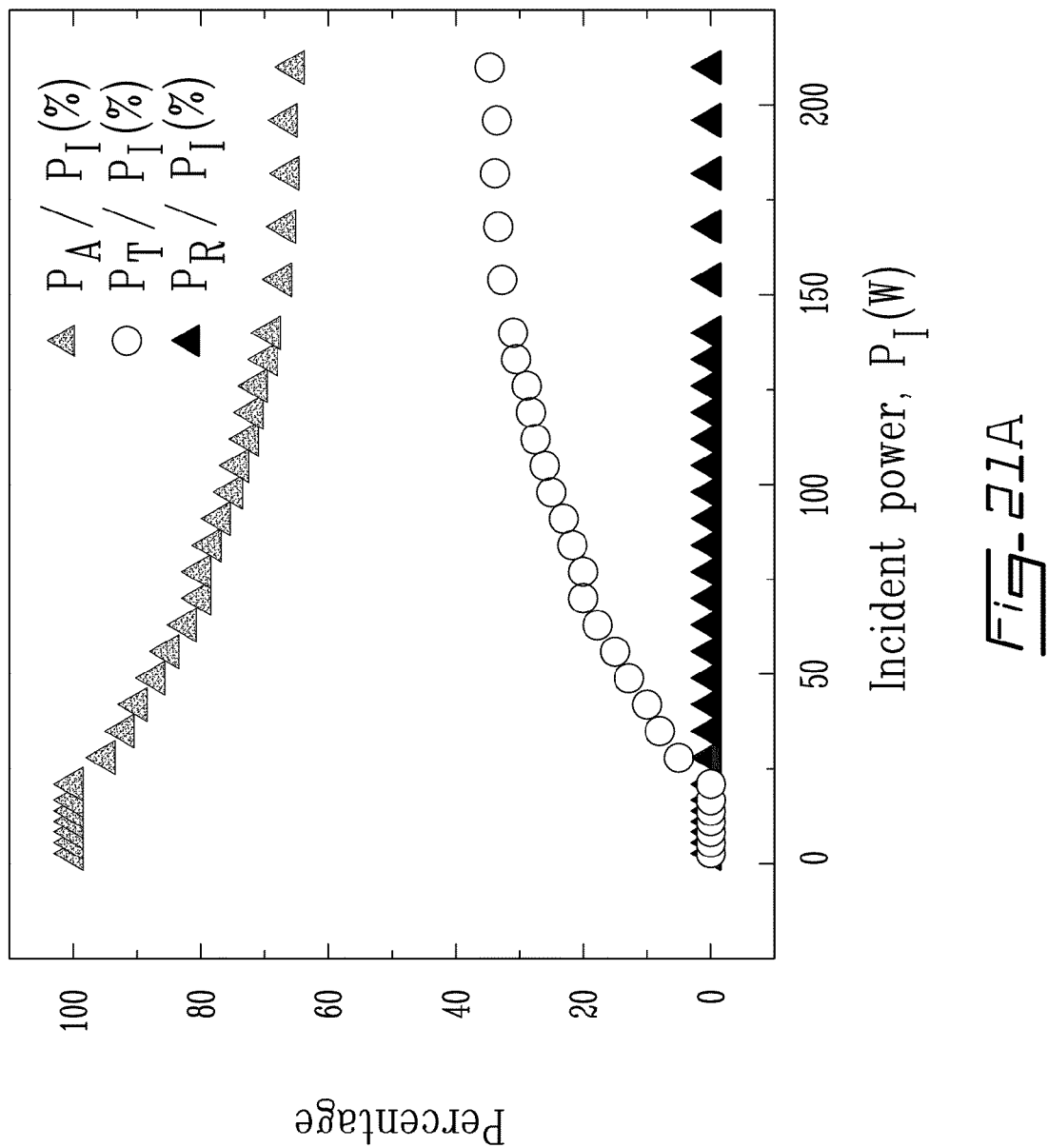
FIG. 21a is a curve showing the percentage of reflected power, $P_R$, transmitted power, $P_T$, and absorbed power, $P_A$, normalized to the incident power, $P_I$, as functions of $P_I$, at 200 MHz, during an experiment carried out with a device according to an embodiment of the present invention and according to an embodiment of a method of the present invention.
Figure 21B:
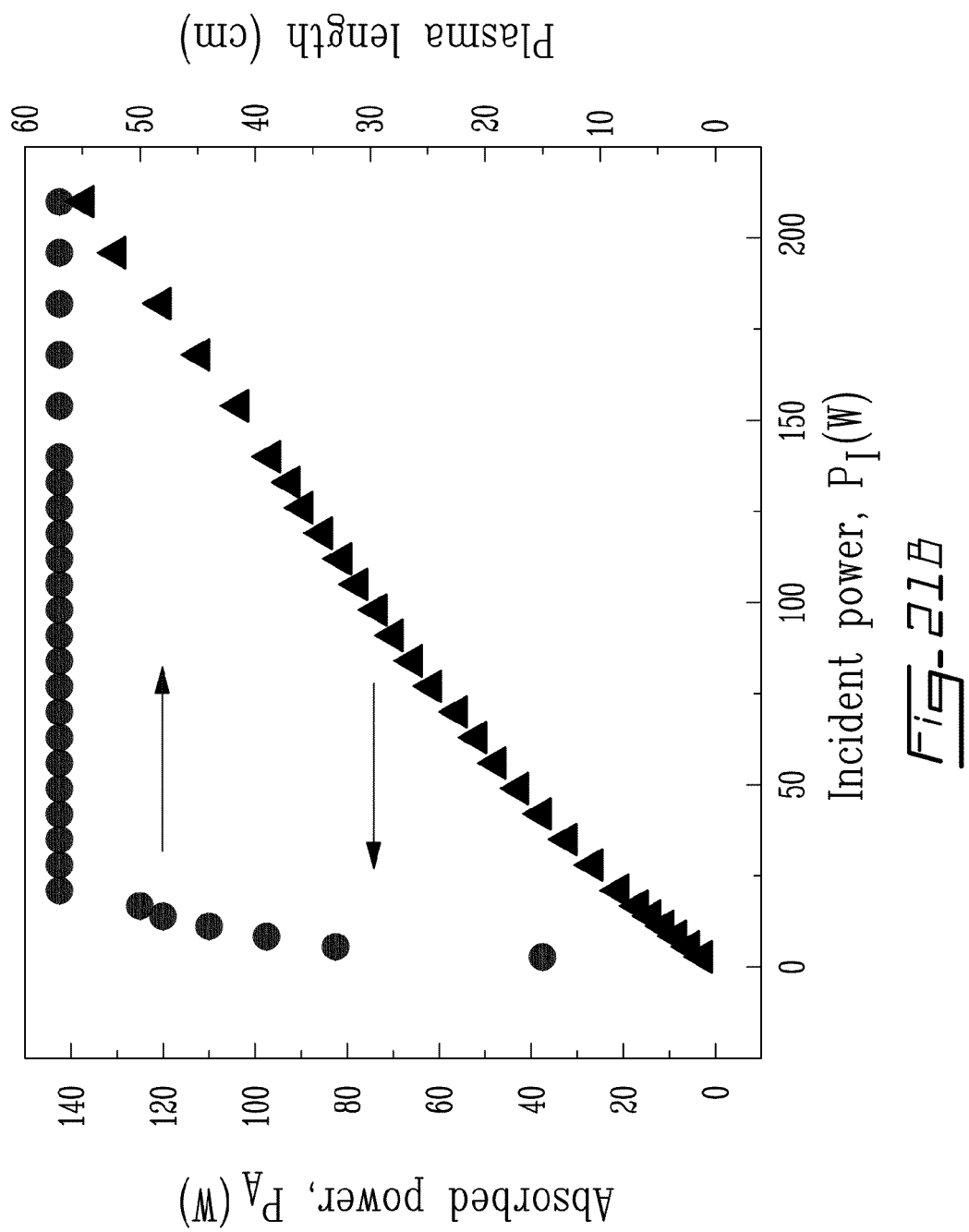
FIG. 21b is a curve showing the power absorbed by the plasma and length of the discharge in the chamber as functions of incident power during an experiment carried out with a device according to an embodiment of the present invention and according to an embodiment of a method of the present invention.

$P_T$ is the power exiting from the applicator and going into the transmission-line terminating matched load. According to an example, carried out with a device of the present invention, power measurements were achieved with the argon gas flow set at 100 sccm at a pressure of 750 mtorr (100 Pa) and with a field frequency of 200 MHz. FIG. 21a displays the corresponding reflected and transmitted powers as functions of the incident power. The percentage of reflected power at the applicator input remained at zero over the whole range of incident HF power tested (0-210 W). As the HF power is raised from 0 to 20 W, the plasma length increases as shown in FIG. 21b; at 20 W, the full applicator length (57 cm) is filled with plasma; at higher incident HF powers, part of the incoming power flows along the field applicator without being absorbed by the discharge and is, in fact, lost in the terminating matched load that prevents reflection at the applicator end. Because of this, above 20 W, there was a continuous decrease of the percentage of power absorbed by the plasma, as shown in FIG. 21a.

Since absorbed power in the discharge remained low (with 50 W of incident power, the density of absorbed power by the plasma is below 10 W/L), gas heating is also low: in fact, the chamber wall and Petri dishes remained, after a few minutes of plasma exposure, at temperatures typically below 40° C. as measured with a thermocouple.

EXAMPLES

The following examples are given merely as an illustration and should not be interpreted as limiting the present invention.

The linear applicator used in the following experiments is similar to the device schematically represented in FIG. 2a. It is a structure of microstrip type, containing a conductive frame of aluminum serving as the ground, a copper or brass strip and a plate of borosilicate glass (Pyrex®). Schematical top and cross section views of this applicator are shown, respectively, in FIGS. 9a and 9b. An N connector 26, placed at the entry of the device, receives the electromagnetic power of a HF generator, operating at 200 MHz. Another N connector 28, placed at the exit of the device, allows for transferring the unused HF power to maintain the plasma to a matched load, thus preventing the power from being reflected at the end of the applicator 910. It should be noted that a Faraday cage 19 (FIG. 9b) makes it possible to avoid any risk of leakage of EM energy to the outside of the microstrip applicator. Its height H (notation defined in FIG. 9b) is much higher than h, so that the electric field which creates and maintains the plasma is almost totally confined to the inside of the chamber where the sterilization takes place. The conducting plate 16 is provided with an aperture 44 for allowing UV measurements by the detector 40 which comprises a window 46 (for example made of $MgF_2$). The device 910 (see FIGS. 9a, 9b, 17 and 18) is also provided with a gas inlet 48 connected to a gas tank (not shown) and a gas outlet 50 connected to a pumping system and an optical collimator 53. The dimensions of the device 910 were as follows (see FIGS. 1a and 9b for reference letters): width (W) of the conducting strip 14=50.8 mm; thickness (t) of the conducting strip 14=3.2 mm; width (L) of the frame 19=146.1 mm; total height of the frame 19=200.5 mm; height h (see FIG. 9b)=50.8 mm; height H (see FIG. 9b)=137.0 mm; thickness of the dielectric plate 20=12.7 mm.

The plasmagenic gas used was highly pure argon at a pressure of 93 Pa and a flow rate of 100 mLsm. The HF power was set at 43 W at the entry of the device. Under these operating conditions, the reflected power was equal to 3 W and the power lost at the end of the line is equal to 10 W. Thus, the power absorbed by the plasma is equal to 30 W.

One makes sure that the intensity of the UV radiation is constant between each experiment by making use of the UV detector 40 (FIG. 9b) in the form of a photomultiplier tube, for example.

Figure 9A:
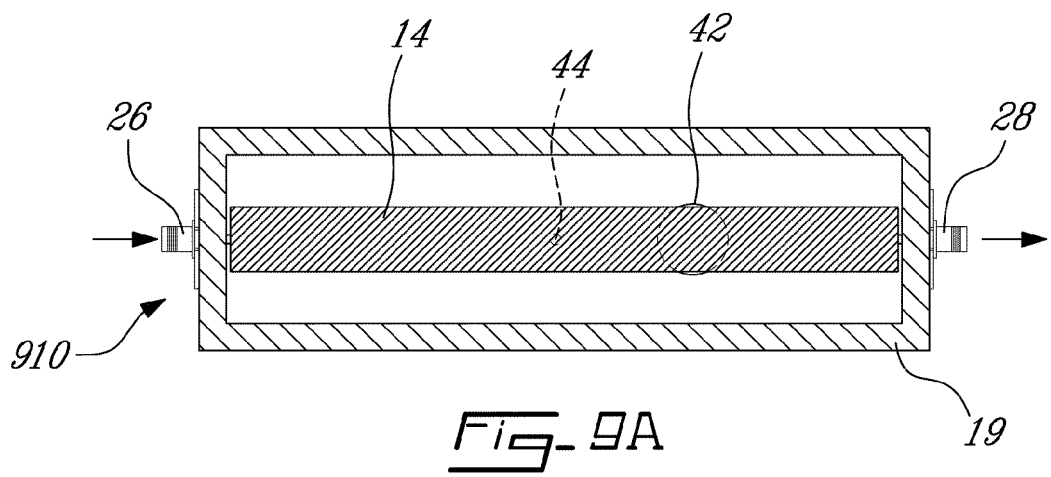
FIG. 9 is a schematic representation of a system of sterilization according to a particular example of the present invention, in a) a top view is presented, and in b) a cross section is presented.
Figure 9B:
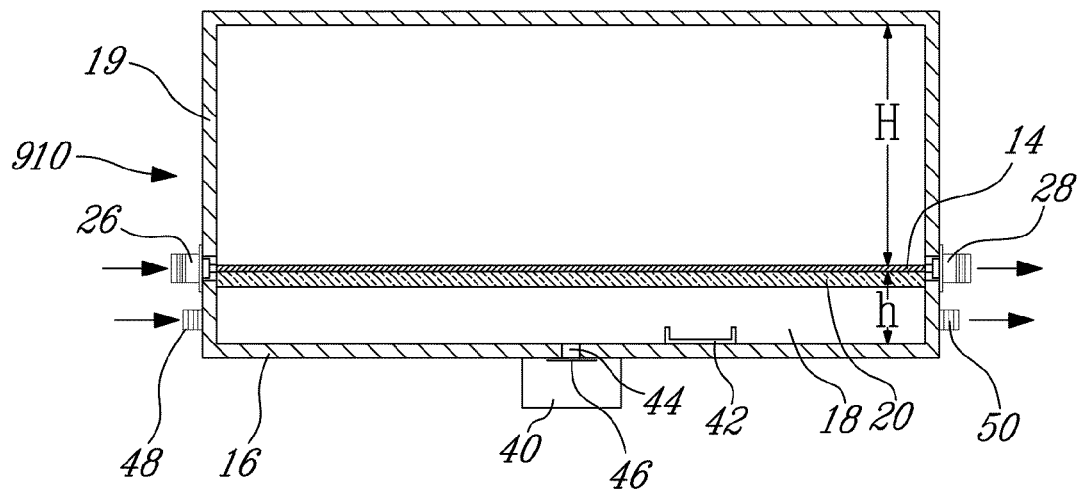
Figure 10:
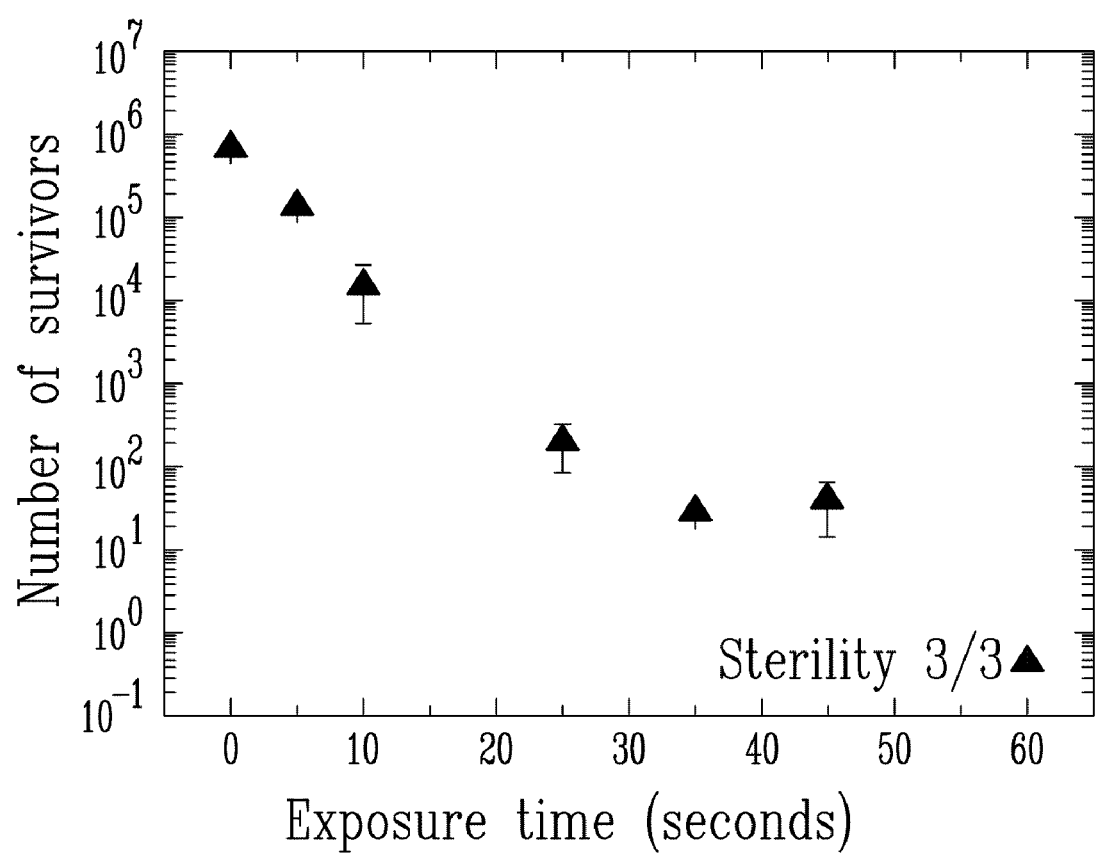
FIG. 10 shows a survival curve of spores of Bacillus atrophaeus obtained as a function of treatment time of a Petri dish with a device such as shown in FIGS. 9a and 9b.

A Petri dish of polystyrene 42 was placed inside the chamber, at the place specified in FIG. 9b. This Petri dish contains 1 million spores of *B. subtilis* (recently renamed *B. atrophaeus*) deposited from a suspension of 100 μl. The corresponding survival curve so obtained is shown in FIG. 10. Three independent experiments were repeated, making it possible to obtain a mean and a standard deviation (error bar) for each of the points. As it can be clearly seen, the 3 Petri dishes were sterilized in 1 minute.

It was observed that the overall time required to reach sterility is function of the amount of stacked spores and their degree of stacking.

Mechanisms of Sterilization

In order to determine which bactericidal species of the argon plasma are responsible for the sterility (see preceding section), the number of spores of *B. subtilis* surviving after 10 seconds of exposure as a function of the incident UV flux (115-195 nm) was plotted (FIG. 10). The UV flux incident on the Petri dish is checked by varying the argon pressure in the chamber between 20 mtorr and 1 torr. In this pressure interval, the UV flux increases as the pressure rises. The other operating conditions (argon flow rate, incident power, location of the Petri dish in the chamber, nature of the deposit of spores) are identical to those described in the preceding section. The UV detector can be placed, for example, beneath the lower metal plate; in this case, the UV rays are collected through an opening 44 (about 1 mm in diameter) pierced through this plate (FIGS. 9a and 9b).

It was mentioned for FIG. 10 that the number of spores surviving (on logarithmic scale) diminishes as a linear function with increasing UV flux (115-195 nm), which shows that the UV rays might be the preponderant bactericidal species when an argon plasma is created in the method of the present invention and under the experimental conditions described in the preceding section. Given that a pure argon plasma at low pressure cannot emit any ray between 115 and 195 nm, it can be envisioned, through without being bound to this hypothesis, that this UV emission results from the presence of impurities (of nitrogen and/or oxygen) inside the sterilization chamber.

Disinfection or Sterilization of Plates in Succession

Figure 12:
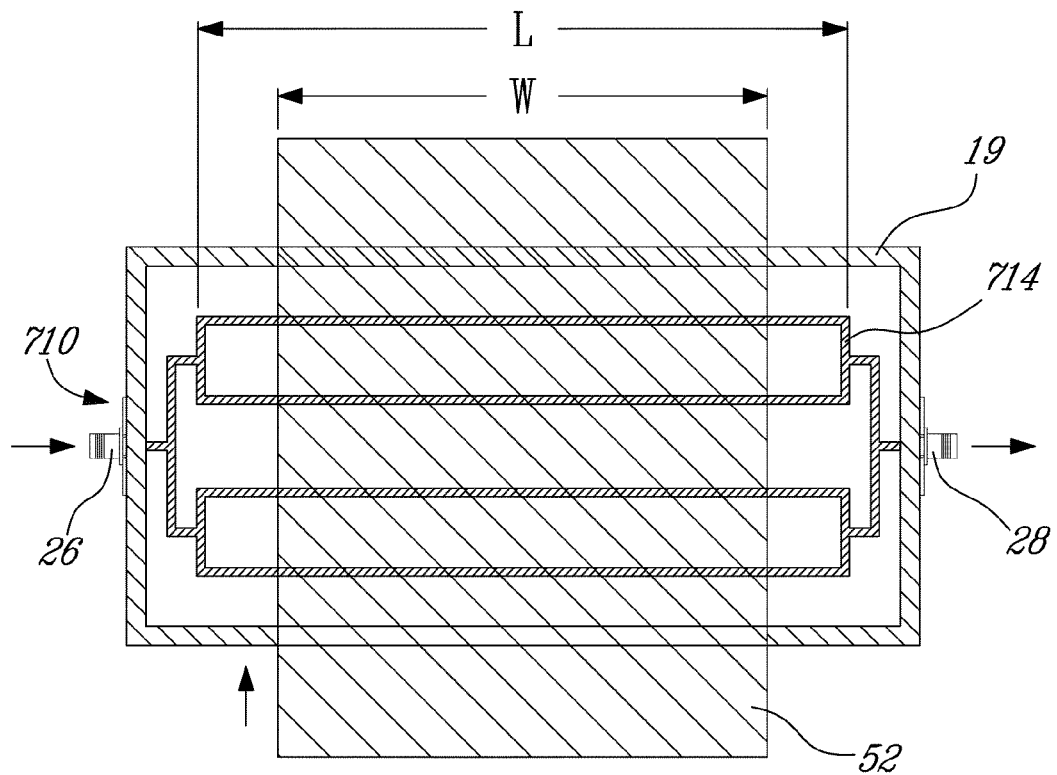
FIG. 12 shows schematically the embodiment of a method of a particular example of the present invention, this figure showing a top view of a linear applicator formed by four conducting strips, energized by a power divider system integrated into the applicator and used to treat a dielectric or conducting plate as it moves past.

Due to their planar geometry, the linear applicators described in the present invention naturally lend themselves to the treatment of plane surfaces. As it can be seen in FIG. 12, a device such as schematically represented in FIG. 6b can be used to perform such a task. The length "L" of the linear applicator 710 is usually larger than the width "W" of the surfaces treated (FIG. 12). Granted that a minimal time is needed for the bactericidal species of the plasma to play their role (about 1 minute, see FIG. 10), the configuration of the applicator should be adapted to the speed of movement of the surfaces being treated. In particular, the incident HF power, the width of the applicator, and the number of conducting strips forming the network (as described in FIG. 12) need to increase when the speed of movement increases, in order to keep a constant time of action for the bactericidal species. More precisely, when the sterilizing agents of the plasma are the UV rays, it is necessary to provide the surfaces being treated with a minimum UV flux to achieve sterility. If the speed of movement is too fast, sterility of the surfaces will not be achieved, and thus one only gets a degree of inactivation of these surfaces (disinfection of more or less high level).

When the object being treated is a dielectric or metal plate such as the plate 52 in FIG. 12, its treatment can be done in the following way.

In the case of a dielectric plate being treated, this will replace the one in FIG. 2a. Thus, a single one of its two surfaces (its lower surface in contact with the plasma) is inactivated or sterilized as it moves past. It should be noted that an interlayer of air may exist between the conducting strip and the dielectric plate to allow for a possible variable thickness of the plate being treated.

In the case of a conductive plate being treated, this will then replace the conducting ground plate of FIG. 2a. A single one of its surfaces (its upper surface in contact with the plasma) is then sterilized as it moves past.

Figure 13:
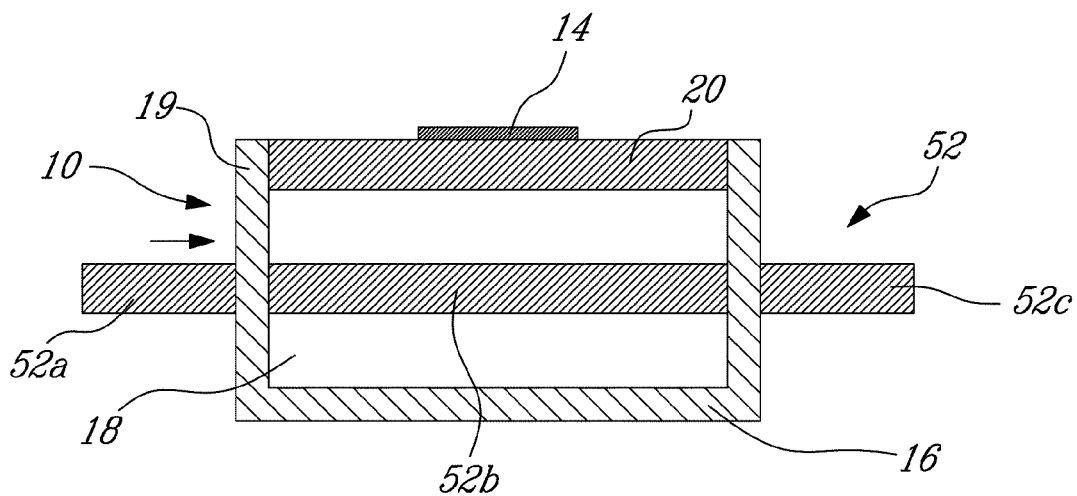
FIG. 13 is a schematical representation of a device for inactivation or sterilization of the two surfaces of a dielectric plate as they move past, according to one particular example of the present invention.
Figure 17:
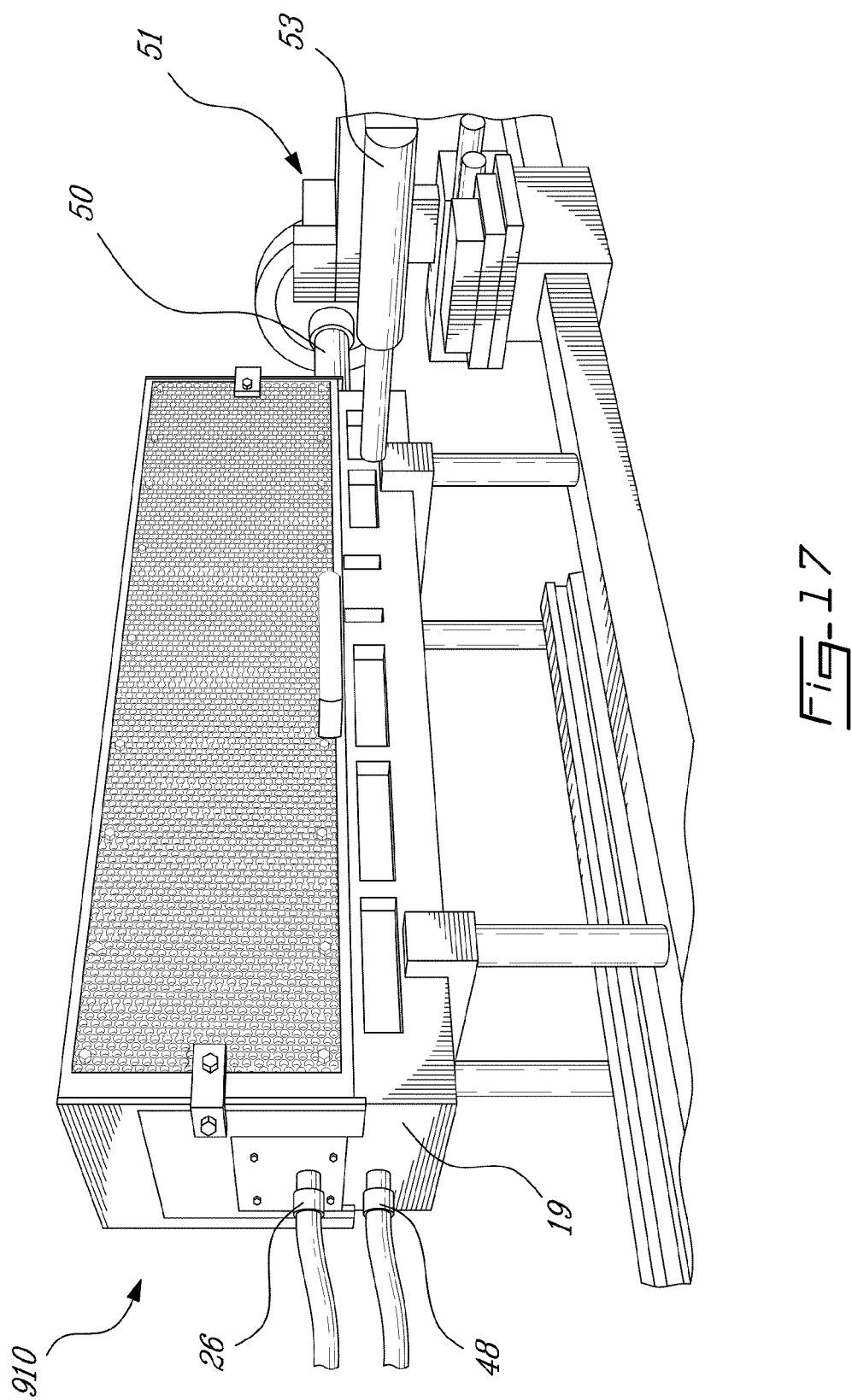
FIG. 17 is a perspective view of a device for inactivation or sterilization according to one particular example of the present invention.
Figure 18:
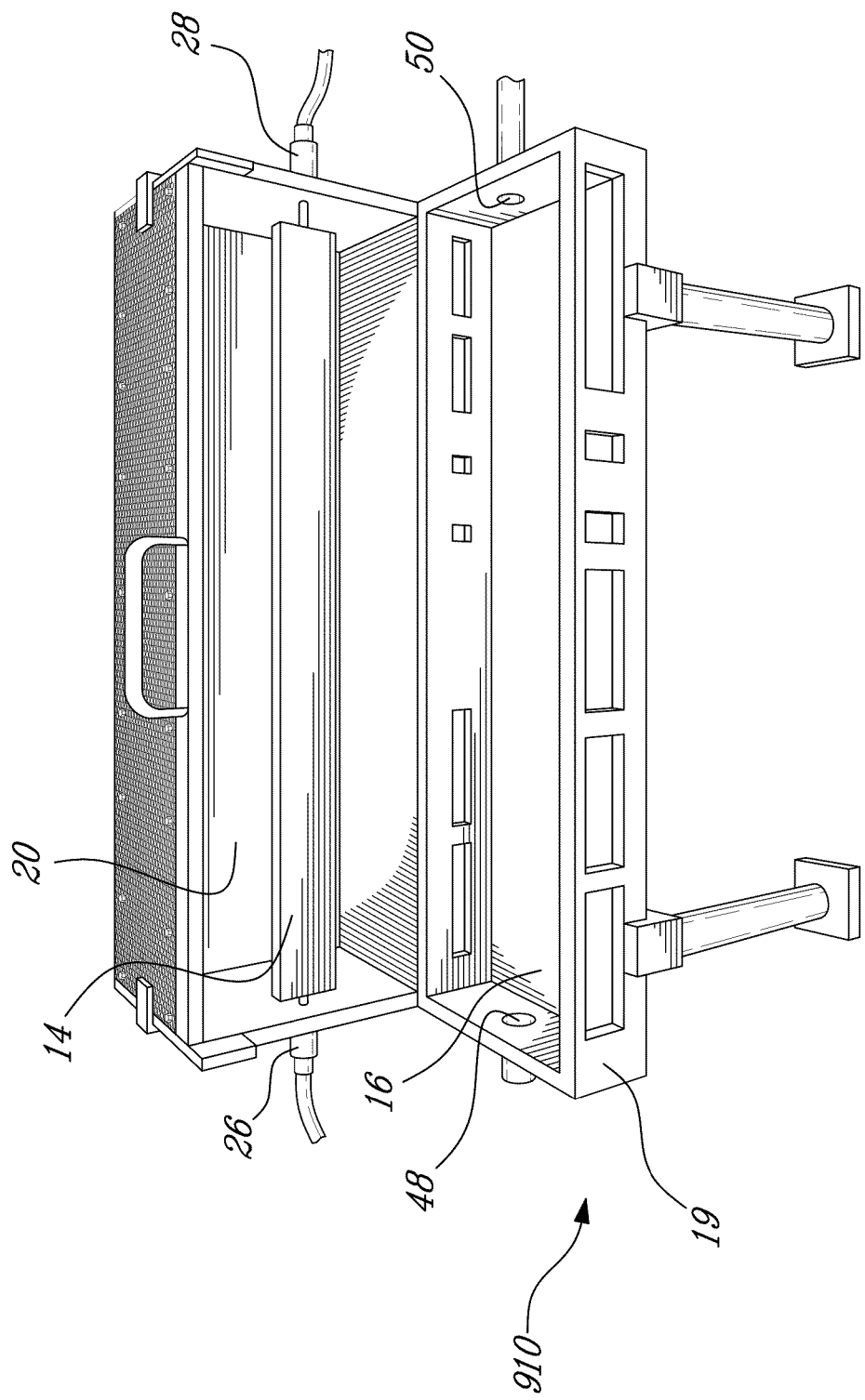
FIG. 18 is another perspective view of the device of FIG. 17, in which the upper pivoting part has been deployed.

In the case when several dielectric and/or conductive plates need to be inactivated or sterilized at the same time, it is advisable to use one of the configurations 2b, 2c or 2d for the treatment:

configuration 2b: 2 dielectric plates and 0 conductive plate;
configuration 2c: 2 dielectric plates and 2 conductive plates;
configuration 2d: 4 dielectric plates and 0 conductive plate;

It is also possible to treat simultaneously the lower surface and the upper surface of a single dielectric plate 52 (FIG. 13) or conducing plate 54 (FIG. 14) such as a metal plate. 52a and 54a represent an untreated portion of the plate, 52b and 54b represent a portion of the plate during treatment, and 52c and 54c represent a portion of the plate after treatment. In FIG. 14 a device 1010 permits to treat the upper surface and then lower surface of a conducting plate 54.

Disinfection or Sterilization of Dielectric Films in Succession

FIG. 15 shows a device 1110 useful for disinfection or sterilization of two surfaces of a dielectric film (such as an agri-food product or a medical packaging film) in succession. The device 1110 comprises a conducting strip 14, a conducting plate 16, a chamber 18 for receiving the film and treating it with a plasma discharge, a dielectric plate 20, a roll 56 comprising the untreated film, and a roll 58 for receiving the sterile or inactivated film. Furthermore, a linear applicator can also be used for the disinfection or sterilization of two dielectric films in succession, being afterwards joined by thermal welding (not shown).

It should be noted that the treatment of packaging films can also be accompanied by the sterilization of three-dimensional objects. In this operating mode, the objects are sterilized outside of their package (FIGS. 7-8). Once the sterilization cycle is over, the objects are packaged in a sterile environment, inside the sterilization chamber or not, as already mentioned in the international application WO2004/050128 page 21.

Direct Sterilization Inside a Dielectric Package

Figure 11:
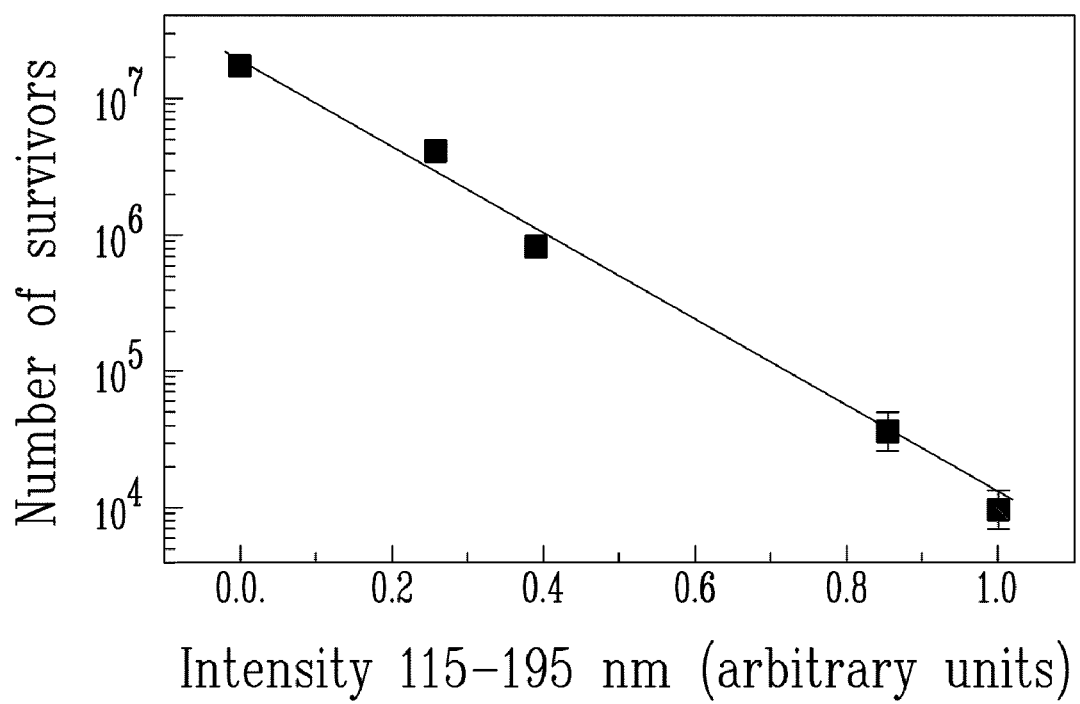
FIG. 11 shows a line expressing the number of surviving spores as a function of the incident UV flux (115-195 nm), after 10 seconds of treatment by a method of a particular example of the present invention, in which a plasma of argon is used, as well as the device shown in FIGS. 9a and 9b.

The sterilization of a three-dimensional object by the present invention can also be realized directly inside a dielectric package. As was previously stipulated (FIG. 11), the method of sterilization described in the present method might result from the bactericidal action of the UV photons. Now, the majority of packages let only a slight proportion of photons pass through their wall. This section describes a method for sterilizing an object situated inside a package and in a reasonable length of time. The method consists in creating the plasma directly inside the package, the latter being formed of a dielectric material transparent to the applied EM field. To do this, the air initially present in the package should first be evacuated and replaced by the plasmagenic gas or gases. The time for this operation depends directly on the porosity of the package, as well as the quality of its seal: the more hermetic the package, the longer it will take.

Furthermore, to create the plasma inside the package, a minimum distance between the object being sterilized and its package needs to be observed. This is due to the existence of a so-called sheath around any object immersed in a plasma. If the package perfectly adheres to the shape of the object with a distance less than one millimeter between the object and its package, the plasma can only be generated with difficulty inside the package. On the other hand, if the package is designed so that a distance of several millimeters is observed between the object and its package, it is possible to create the plasma inside the package (FIG. 16). As shown in FIG. 16, an object 60 disposed in its package 62 can be sterilized or inactivated in the device 10. It can be seen that there is a significant volume between 63 the package 62 and the object 60 in order to create a plasma therebetween.

For example, a package made up of two parts: one made of semirigid dielectric material (such as Teflon), possibly recyclable, and the other of a flexible material, such as a disposable packaging paper (e.g. Kimguard®), can be used.

Erosion-Free Treatment of Surfaces

As previously indicated, the plasma sterilization process must not only efficiently inactivate micro-organisms, but also it should not induce damage to the exposed surfaces. In particular, as many medical devices (MDs) comprise polymers, the etching of polymers should be as limited as possible. Polystyrene microspheres (PS, approximately one micrometer in diameter) were used in order to evaluate the level of damage induced by the method and device of the present invention to contaminated objects. Such PS microspheres have already been employed to compare damage caused by the early and the late $N_2$—$O_2$ discharge afterglows (Boudam et al. *J. Phys. D: Appl. Phys.* 40 1694-1711). These microspheres were then found to be quite responsive to various plasma species: the observed off-axis erosion rate correlated with the increase of the O atom density in the afterglow as the $O_2$ percentage is increased, while the on-axis erosion observed at 0% $O_2$ appeared related to the action of both the $N_2$ metastable molecules and the $N_2^+$ ions. Similar PS microspheres were also employed by Lerouge et al. in *Journal of Biomedical and Material Research* 51 128-135 so as to demonstrate that the high sporicidal efficacy provided by their $O_2/CF_4$ plasma was related to its high etch rate of polymers. Bretagnol et al. in *Plasma processes and polymers* 3 443-445 also reported that PS microspheres can strongly be etched by an $O_2$ plasma.

Figures 22A, 22B:
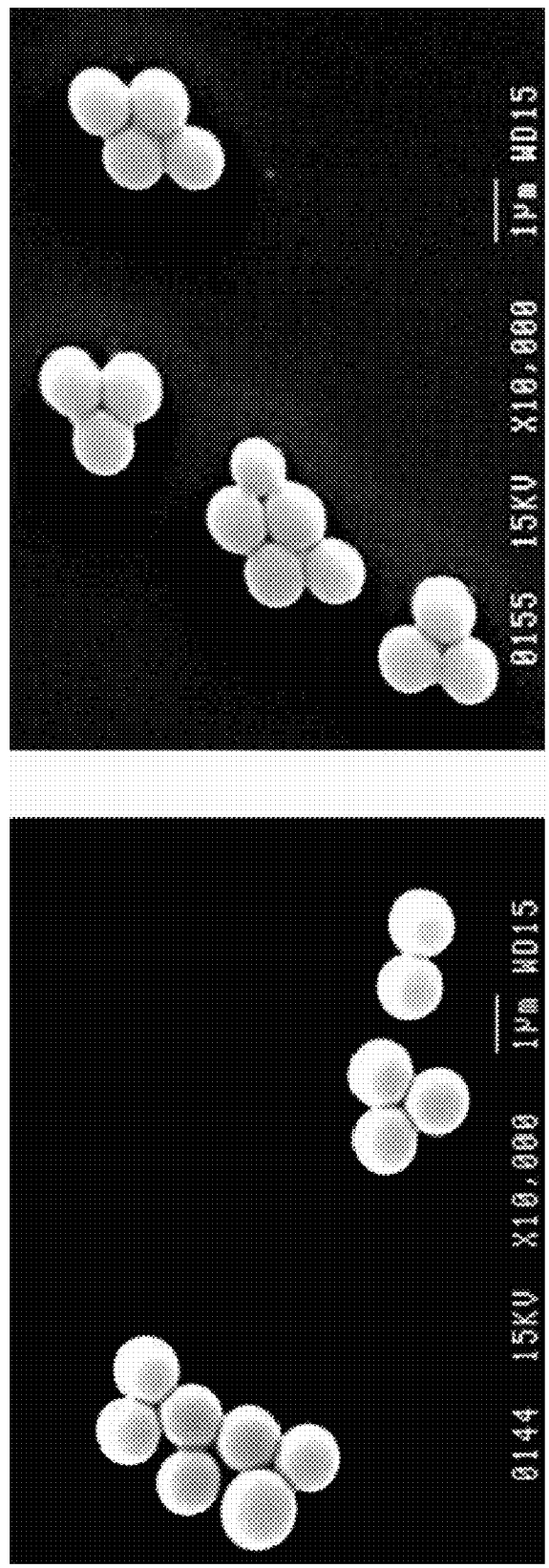

FIG. 22a shows SEM micrographs of PS microspheres before treatment. These microspheres were then deposited on Petri dishes, located in the planar discharge as shown in FIGS. 9a and 9b, and subjected for 1 minute to an argon plasma. The gas flow was 100 sccm at a gas pressure of 750 mtorr. Under these operating conditions, all the spores of a $10^6$ deposit were inactivated, as shown in FIG. 10. As it can be seen in FIG. 22b, the exposed microspheres were not disrupted or eroded. The absence of etching damage here contrasts with plasma sterilization techniques based on the action of radicals. It was thus demonstrated that the method and device of the present invention permit inactivation and/or sterilization without however substantially damaging or degrading the treated surface(s).

Although the present invention has been described with the help of specific examples, it is understood that many variations and modifications can be grafted onto these examples, and the present invention aims to cover such modifications, usages or adaptations of the present invention generally following the principles of the invention and including every variation of the present specification that will become known or conventional in the field of activity where the present invention lies, in accordance with the scope of the following claims.

The invention claimed is:

1. A method of sterilization and/or inactivation of at least one surface of at least one contaminated object, said method comprising submitting said at least one surface to a plasma discharge generated from an applicator of electromagnetic field of linear type, the plasma having a temperature below 80° C, and having an absorbed power per unit of volume of plasma of less than 20 W/L, so as to sterilize and/or inactivate said at least one surface without substantially degrading it, wherein said at least one contaminated object is a dielectric film, and wherein said film is sterilized as it is rolled off a roll, said film entering a chamber of the applicator at a predetermined height, then leaving said chamber without interrupting the sterilization process or the electromagnetic field serving to maintain said plasma, two surfaces of said dielectric film are then inactivated and/or sterilized simultaneously under the action of bactericidal species of the plasma.

2. The method of claim 1, wherein said surface are sterilized after having been subjected to the discharge of said plasma for a period of less than 10 minutes.

3. The method of claim 1, wherein said surface are sterilized after having been subjected to the discharge of said plasma for a period of less than 1 minute.

4. The method of claim 1, wherein the temperature of said plasma is less than 40° C.

5. The method of claim 1, wherein the temperature of said plasma is less than 30° C.

6. The method of claim 1, wherein the absorbed power per unit volume of plasma is less than 15 W/L.

7. The method of claim 1, wherein the absorbed power per unit volume of plasma is less than 5 W/L.

8. The method of claim 1, wherein, after a predetermined period of time, a power input and output of the applicator of electromagnetic field of linear type are reversed so as to achieve a uniform treatment of said surfaces.

9. The method of claim 1, wherein said plasma comprises at least one rare gas.

10. The method of claim 1, wherein said plasma comprises at least one gas chosen from $N_2$, $CO_2$, $O_2$ and mixtures thereof.

11. A method of sterilization and/or inactivation of at least one surface of at least one contaminated object, said method comprising submitting said at least one surface to a plasma discharge generated from an applicator of electromagnetic field of linear type, the plasma having a temperature below 80° C., and having an absorbed power per unit of volume of plasma of less than 20 W/L, so as to sterilize and/or inactivate said at least one surface without substantially degrading it, wherein said at least one contaminated object being treated is a metal plate, moving past said applicator, so that a lower surface and an upper surface of the plate are inactivated or sterilized at the same time.

12. The method of claim 11, wherein said sterilization and/or inactivation is carried out in a chamber, and wherein at least one wall defining said chamber comprises at least one aperture so as to simultaneously permit treatment of at least one other object disposed outside of said chamber by means of a flowing afterglow of said plasma.

13. The method of claim 11, wherein said lower and upper surfaces are sterilized after having been subjected to the discharge of said plasma for a period of less than 10 minutes.

14. The method of claim 13, wherein the absorbed power per unit volume of plasma is less than 15 W/L.

15. The method of claim 11, wherein said lower and upper surfaces are sterilized after having been subjected to the discharge of said plasma for a period of less than 1 minute.

16. The method of claim 15, wherein the temperature of said plasma is less than 30° C.

17. A method of sterilization and/or inactivation of at least one surface of at least one contaminated object, said method comprising submitting said at least one surface to a plasma discharge generated from an applicator of electromagnetic field of linear type, the plasma having a temperature below 80° C., and having an absorbed power per unit of volume of plasma of less than 20 W/L, wherein said at least one contaminated object is polystyrene micro-spheres and said method permits an erosion-free sterilization and/or inactivation of said polystyrene micro-spheres, as determined by observing the sterilized and/or inactivated polystyrene micro-spheres by means of Scanning Electron Microscopy as compared to said polystyrene micro-spheres before sterilization and/or inactivation.

18. The method of claim 17, wherein said at least one surface is treated in succession as they are introduced into said applicator.

19. The method of claim 17, wherein said object is sterilized directly inside its package, said plasma being created outside the object, as well as in a sufficient volume included between the package and the object.

20. The method of claim 17, wherein said at least one surface is sterilized after having been subjected to the discharge of said plasma for a period of less than 10 minutes.

21. The method of claim 17, wherein said at least one surface is sterilized after having been subjected to the discharge of said at least one plasma for a period of less than 1 minute.

22. The method of claim 21, wherein the temperature of said plasma is less than 30° C.

* * * * *